United States Patent
Wang

(10) Patent No.: US 10,842,728 B2
(45) Date of Patent: *Nov. 24, 2020

(54) LIGHT-ABSORBING COMPOSITIONS AND METHODS OF USE

(71) Applicant: Allele Biotechnology & Pharmaceuticals, Inc., San Diego, CA (US)

(72) Inventor: Jiwu Wang, La Jolla, CA (US)

(73) Assignee: Allele Biotechnology & Pharmaceuticals, Inc., San Diego, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/682,388

(22) Filed: Aug. 21, 2017

(65) Prior Publication Data

US 2018/0049962 A1 Feb. 22, 2018

Related U.S. Application Data

(63) Continuation-in-part of application No. 14/961,678, filed on Dec. 7, 2015, now Pat. No. 9,737,472, which is a continuation-in-part of application No. 13/206,420, filed on Aug. 9, 2011, now Pat. No. 9,205,284.

(60) Provisional application No. 61/371,741, filed on Aug. 9, 2010.

(51) Int. Cl.
| | | |
|---|---|---|
| A61K 8/64 | (2006.01) | |
| A61Q 17/04 | (2006.01) | |
| A61K 8/98 | (2006.01) | |
| C07K 14/435 | (2006.01) | |
| A61K 38/17 | (2006.01) | |
| A61K 49/00 | (2006.01) | |

(52) U.S. Cl.
CPC ............... *A61K 8/64* (2013.01); *A61K 8/987* (2013.01); *A61K 38/1767* (2013.01); *A61Q 17/04* (2013.01); *C07K 14/43504* (2013.01); *A61K 49/0045* (2013.01); *A61K 2800/434* (2013.01); *C09C 2210/50* (2013.01)

(58) Field of Classification Search
CPC ...... A61K 9/0014; A61K 38/00; A61K 35/36; A61K 2039/6031; A61K 2800/43; A61K 38/164; A61P 17/00; C07K 14/195; A61L 27/54; A61L 27/60; A61L 2300/252; A61L 27/362
See application file for complete search history.

(56) References Cited

U.S. PATENT DOCUMENTS

| | | | |
|---|---|---|---|
| 1,985,424 A | 12/1934 | Piggott | |
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Kosmin | |
| 2,703,798 A | 3/1955 | Schwartz | |
| 2,826,551 A | 3/1958 | Geen | |
| 2,965,576 A | 12/1960 | Wilson | |
| 3,155,591 A | 11/1964 | Hilfer | |
| 3,332,880 A | 7/1967 | Kessler et al. | |
| 3,755,560 A | 8/1973 | Dickert et al. | |
| 3,929,678 A | 12/1975 | Laughlin et al. | |
| 3,958,581 A | 5/1976 | Abegg et al. | |
| 3,959,461 A | 5/1976 | Bailey et al. | |
| 3,962,418 A | 6/1976 | Birkofer | |
| 3,964,500 A | 6/1976 | Drakoff | |
| 4,152,416 A | 5/1979 | Spitzer et al. | |
| 4,202,879 A | 5/1980 | Shelton | |
| 4,364,837 A | 12/1982 | Pader | |
| 4,387,090 A | 6/1983 | Bolich, Jr. | |
| 4,421,769 A | 12/1983 | Dixon et al. | |
| 4,557,853 A | 12/1985 | Collins | |
| 4,599,379 A | 7/1986 | Flesher et al. | |
| 4,628,078 A | 12/1986 | Glover et al. | |
| 4,677,120 A | 6/1987 | Parish et al. | |
| 4,741,855 A | 5/1988 | Grote et al. | |
| 4,800,197 A | 1/1989 | Kowcz et al. | |
| 4,816,261 A | 3/1989 | Luebbe et al. | |
| 4,835,206 A | 5/1989 | Farrar et al. | |
| 4,849,484 A | 7/1989 | Heard | |
| 4,885,311 A | 12/1989 | Parish et al. | |
| 4,960,764 A | 10/1990 | Figueroa, Jr. et al. | |

(Continued)

FOREIGN PATENT DOCUMENTS

| | | |
|---|---|---|
| EP | 228868 A3 | 7/1987 |
| EP | 330369 A1 | 2/1989 |

(Continued)

OTHER PUBLICATIONS

Zimmer et al. Green fluorescent protein (GFP): applications, structure, and related photophysical behavior. Chem. Rev. 2002, 102, 759-781. (Year: 2002).*

(Continued)

*Primary Examiner* — Soren Harward
*Assistant Examiner* — Jia-Hai Lee
(74) *Attorney, Agent, or Firm* — Duane Morris LLP

(57) ABSTRACT

The present disclosure relates to methods and compositions comprising naturally occurring light absorbing molecules for preventing damages from light exposure. Specific embodiments of this disclosure include fluorescent proteins from *Brachiostoma lanceolatum*.

11 Claims, 9 Drawing Sheets
(5 of 9 Drawing Sheet(s) Filed in Color)
Specification includes a Sequence Listing.

(56) References Cited

U.S. PATENT DOCUMENTS

| | | | |
|---|---|---|---|
| 4,970,252 | A | 11/1990 | Sakuta et al. |
| 4,976,953 | A | 12/1990 | Orr et al. |
| 5,011,681 | A | 4/1991 | Ciotti et al. |
| 5,049,584 | A | 9/1991 | Purcell et al. |
| 5,073,371 | A | 12/1991 | Turner et al. |
| 5,073,372 | A | 12/1991 | Turner et al. |
| 5,100,660 | A | 3/1992 | Hawe et al. |
| 5,104,646 | A | 4/1992 | Bolich, Jr. et al. |
| 5,106,609 | A | 4/1992 | Bolich, Jr. et al. |
| 5,120,532 | A | 6/1992 | Wells et al. |
| 5,124,356 | A | 6/1992 | Purcell et al. |
| RE34,075 | E | 9/1992 | Purcell et al. |
| 5,151,209 | A | 9/1992 | McCall et al. |
| 5,151,210 | A | 9/1992 | Steuri et al. |
| RE34,584 | E | 4/1994 | Grote et al. |
| 5,412,004 | A | 5/1995 | Tachibana et al. |
| 5,652,228 | A | 7/1997 | Bissett |
| 5,654,362 | A | 8/1997 | Schulz, Jr. et al. |
| 5,681,852 | A | 10/1997 | Bissett |
| 5,686,082 | A | 11/1997 | N'Guyen |
| 5,695,747 | A | 12/1997 | Forestier et al. |
| 5,760,116 | A | 6/1998 | Kilgour et al. |
| 5,795,565 | A | 8/1998 | Eteve et al. |
| 5,811,487 | A | 9/1998 | Schulz, Jr. et al. |
| 5,837,793 | A | 11/1998 | Harashima et al. |
| 6,159,485 | A | 12/2000 | Yu et al. |
| 9,205,284 | B2 * | 12/2015 | Wang ............ A61K 8/64 |
| 9,737,472 | B2 * | 8/2017 | Wang ............ A61K 8/64 |
| 2005/0036961 | A1 | 2/2005 | Hansenne et al. |
| 2007/0134703 | A1 * | 6/2007 | Lukyanov ...... C07K 14/43504 435/6.16 |
| 2012/0093737 | A1 | 4/2012 | Wang |
| 2013/0344591 | A1 | 12/2013 | Lukyanov et al. |
| 2016/0193132 | A1 | 7/2016 | Wang |

FOREIGN PATENT DOCUMENTS

| | | |
|---|---|---|
| EP | A-0-518772 A1 | 5/1992 |
| EP | A-0-518773 A1 | 6/1992 |
| FR | 2781231 | 1/2000 |
| FR | 2788058 | 7/2000 |
| GB | 849433 | 9/1980 |
| GB | 2274585 A | 8/1994 |
| WO | WO-96/33689 A1 | 10/1996 |
| WO | WO-00/04047 A1 | 1/2000 |
| WO | WO-00/40611 A1 | 7/2000 |
| WO | WO 2000/46233 | 8/2000 |
| WO | WO-02/066668 A2 | 8/2002 |
| WO | WO 2007/142582 A1 | 12/2007 |
| WO | WO 2007142582 * | 12/2007 ........... C07K 14/435 |
| WO | WO-09/076423 A2 | 6/2009 |

OTHER PUBLICATIONS

Ai et al., "Directed evolution of a monomeric, bright and photostable version of Clavularia cyan fluorescent protein: structural characterization and applications in fluorescence imaging," Biochem J., 2006, 400(3):531-540.

Ai et al., "Hue-shifted monomeric variants of Clavularia cyan fluorescent protein: identification of the molecular determinants of color and applications in fluorescence imaging," BMC Biol., Mar. 6, 2008, 6:13, 13 pages.

Altschul, "A Protein Alignment Scoring System Sensitive at All Evolutionary Distances," J. Mol. Evol., 1993, 36:290-300.

Altschul et al., "Basic Local Alignment Search Tool," J. Mol. Biol., 1990, 215:403-410.

Bomati et al., "Amphioxus encodes the largest known family of green fluorescent proteins, which have diversified into distinct functional classes," BMC Evol. Biol., 2009, 9:77, 11 pages.

Botta et al., "Genotoxicity of visible light (400-800 nm) and photoprotection assessment of ectoin, L-ergothioneine and mannitol and four sunscreens," J. Photochem. Photobiol. B: Biology, 2008, 91(1):24-34.

Bou-Abdallah et al., "Quenching of superoxide radicals by green fluorescent protein," Biochim. Biophys. Acta, 2006, 1760(11):1690-1695.

Deheyn et al., "Endogenous green fluorescent protein (GFP) in amphioxus," Biol. Bull., Oct. 2007, 213(2):95-100.

Devereux et al., "A comprehensive set of sequence analysis programs for the V A X," Nucleic Acids Research, 1984, 12(1):387-395.

Henikoff et al., "Amino acid substitution matrices from protein blocks," Nov. 1992, Proc. Natl. Acad. Sci. USA 89:10915-10919.

Hoi et al., "A Monomeric Photoconvertible Fluorescent Protein for Imaging of Dynamic Protein Localization," J. Mol. Biol., 2010, 401:776-791.

Karlin et al., "Applications and statistics for multiple high-scoring segments in molecular sequences," Proc. Natl. Acad. Sci. USA, Jun. 1993, 90:5873-5787.

Pleasance et al., "A comprehensive catalogue of somatic mutations from a human cancer genome," Nature, Jan. 14, 2010, 463(7278):191-196.

Vainio et al., "An International Evaluation of the Cancer-Preventive Potential of Sunscreens," Int. J. Cancer 88, 838-842 (2000).

Zimmer, Green Fluorescent Protein (GFP): Applications, Structure, and Related Photophysical Behavior. Chem. Rev. 2002, 102, 759,781.

International Search Report and Written Opinion in International Application No. PCT/US18/47390, dated Nov. 2, 2018, in 8 pages.

* cited by examiner

FIG. 1. Test of the stability of FPs at room temperature (RT) for 18 months
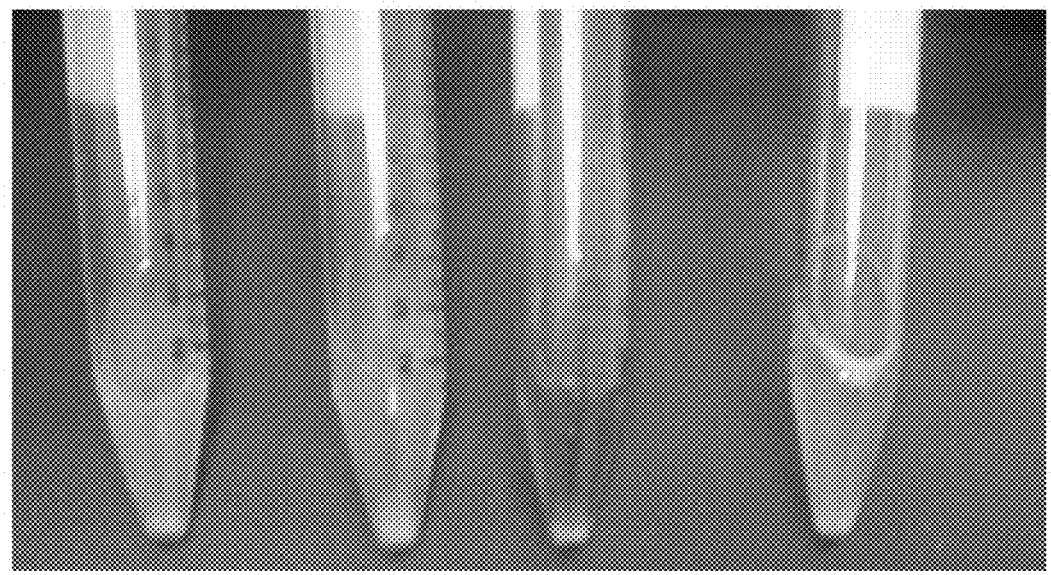

FIG. 2. Production of recombinant LanYFP and LanRFP
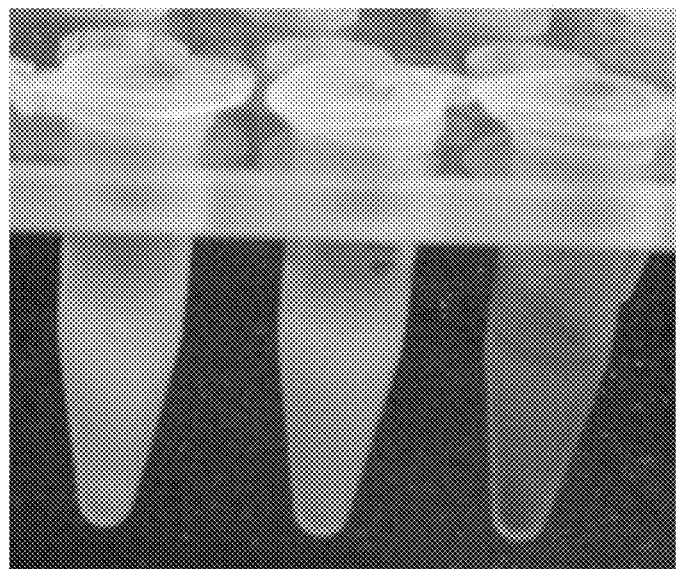

FIG. 3. Recombinant LanYFP and LanRFP are stable and remain tetrameric in SDS-PAGE gel.
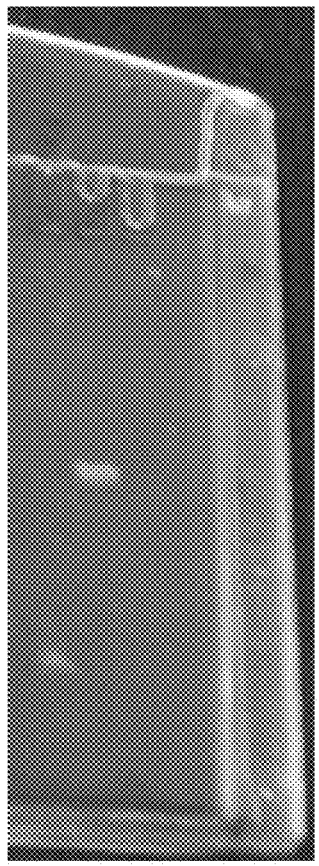

FIG. 4. Formation of heteratetramers between LanYFP and LanRFP
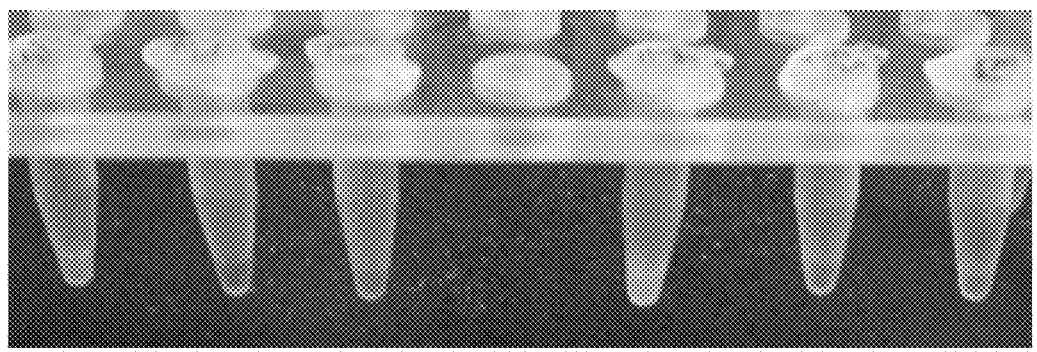

FIG. 5. Protection of cells by fluorescent proteins from UV damage
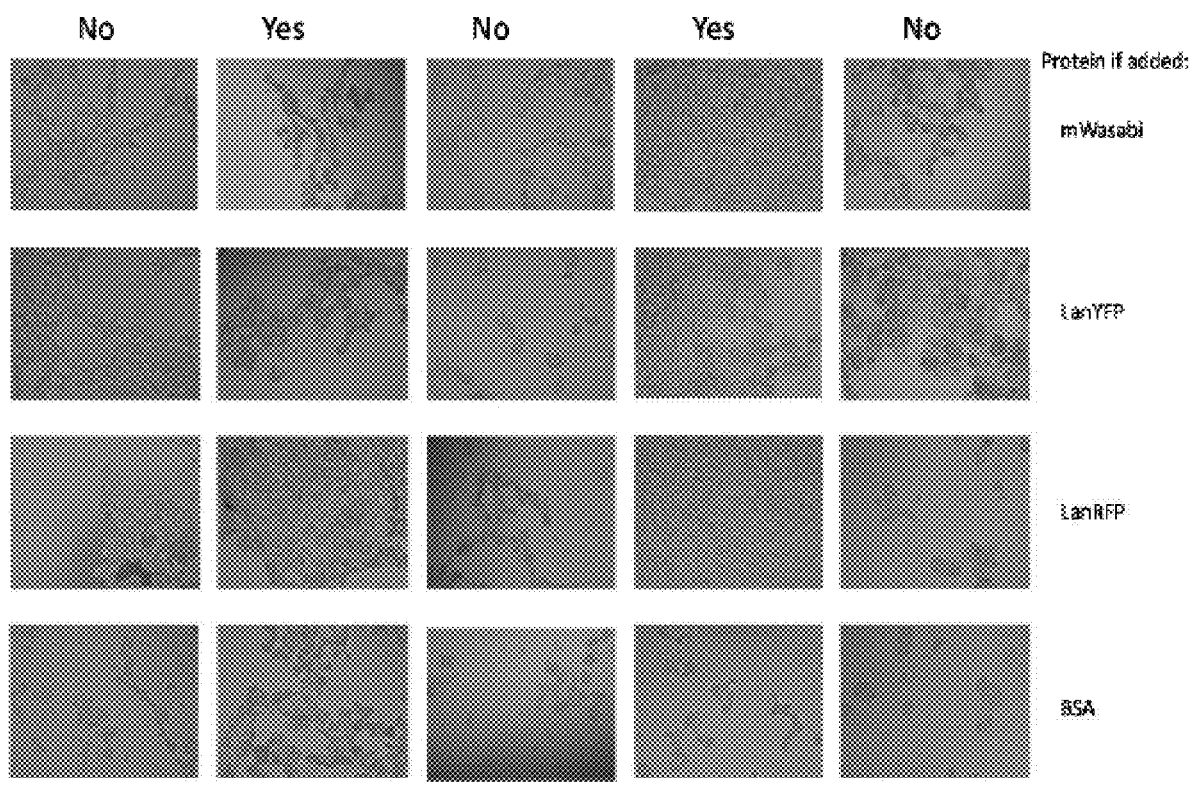

FIG. 6A:

SEQ ID No 1. LanYFP sequence for E. coli expression as tetramers (with cloning tag)

atggtgagcaagggcgaggaggataacatggcctctctcccagcgacacatgagttacacatctttggctccttcaacggtgtggactttga
catggtgggtcgtggcaccggcaatccaaatgatggttatgaggagttaaacctgaagtccaccaagggtgccctccagttctccccctgga
tTctggtccctcaaatcgggtatggcttccatcagtacctgcccttccccgacgggatgtcgcctttccaggccgccatgaaagatggctcc
ggataccaagtccatcgcacaatgcagtttgaagacggtgcctccctgacttccaactaccgctacacctacgagggaagccacatcaaag
gagagtttcaggtgatcgggactggtttccctgctgacggtcctgtgatgaccaactcgctgaccgctgcggactggtgcgtgaccaagatg
ctgtacccaacgacaaaaccatcatcagcacctttgactggacttacaccactggaagtggcaagcgctaccagagcacagtgcggacc
aactacacctttgccaagccaatggcggccaacatcctgaagaaccagccgatgttcgtgttccgtaagacggagctcaagcactccaaga
ccgagctcaacttcaaggagtggcaaaaggcctttaccgatgtgatgggcatggacgagctgtacaag

FIG. 6B:

SEQ ID No 2. LanRFP sequence for E. coli expression as tetramers (with cloning tag)

atggtgagcaagggcgaggaggataacatggcccctctcccagcaacccacgatttacacatctccggctcaatcaatggacatgagtttg
acttggaaggcagtggcaagggcaatgcaaaagaaggttatcaggagctccacctaaagtccaacaagggtgacctgtcattctcccctg
gatTctggtcccaaacatcggctacggcttctaccagtacctgcccttccccgacggagcgatgtcgccttaccaggccgccatgcacgat
ggctccggatacgtgatgcatcgttcaatgcagtttgaggatggtgccatgctgcattcagaccaccgctacatctataagggaaaccatatc
aaaggagagtttcggctgaccggaagcggtttccctgctgacggccctgtgatgaccaactcgctgaccgctgcggactggtgcgtcgac
aagctgctgtacccaaacgacaacaccataatcggcaaattcgactggacctacaccactaccagtggcaagcgctaccaaagtgatgtgc
agaccaacgtcacatttggcaagccaatagcggccgacattttgaagaagcagccaatgttcgtgttccgcaaggtggaactcaagcacac
caagactgagctcaacttcaagcagtggcagaaggcattccaggacatcgccggcatggacgagctgtacaagtaattaatgcag

FIG. 7A:

SEQ ID No. 3: Translation of SEQ ID No 1. LanYFP sequence for E. coli expression as tetramers (with cloning tag):

MVSKGEEDNMASLPATHELHIFGSFNGVDFDMVGRGTGNPNDGYEELNLKSTKGALQF
    SPWILVPQIGYGFHQYLPFPDGMSPFQAAMKDGSGYQVHRTMQFEDGASLTSNY
    RYTYEGSHIKGEFQVIGTGFPADGPVMTNSLTAADWCVTKMLYPNDKTIISTFD
    WTYTTGSGKRYQSTVRTNYTFAKPMAANILKNQPMFVFRKTELKHSKTELNFKE
    WQKAFTDVMGMDELYK

FIG. 7B:

SEQ ID No. 4: Translation of SEQ ID No 2. LanRFP sequence for E. coli expression as tetramers (with cloning tag):

MVSKGEEDNMAPLPATHDLHISGSINGHEFDLEGSGKGNAKEGYQELHLKSNKGDLSFS
    PWILVPNIGYGFYQYLPFPDGAMSPYQAAMHDGSGYVMHRSMQFEDGAMLHS
    DHRYIYKGNHIKGEFRLTGSGFPADGPVMTNSLTAADWCVDKLLYPNDNTIIGK
    FDWTYTTTSGKRYQSDVQTNVTFGKPIAADILKKQPMFVFRKVELKHTKTELNF
    KQWQKAFQDIAGMDELYK

FIG. 8A:

SEQ ID No. 9: LanYFP sequence for E. coli expression as tetramers tctctcccagcgacacatgagttacacatctttggctccttcaacggtgtggactttgacatggtgggtcgtggcaccggcaatccaaatgatg
gttatgaggagttaaacctgaagtccaccaagggtgccctccagttctcccectggatTctggtccctcaaatcgggtatggcttccatcagt
acctgcccttccccgacgggatgtcgcctttccaggccgccatgaaagatggctccggataccaagtccatcgcacaatgcagtttgaaga
cggtgcctccctgacttccaactaccgctacacctacgagggaagccacatcaaaggagagtttcaggtgatcgggactggtttccctgctg
acggtcctgtgatgaccaactcgctgaccgctgcggactggtgcgtgaccaagatgctgtaccccaacgacaaaaccatcatcagcacctt
tgactggacttacaccactggaagtggcaagcgctaccagagcacagtgcggaccaactacacctttgccaagccaatggcggccaacat
cctgaagaaccagccgatgttcgtgttccgtaagacggagctcaagcactccaagaccgagctcaacttcaaggagtggcaaaaggccttt
accgatgtgatgggcatggacgagctgtacaag

FIG. 8B:

SEQ ID No. 10: LanRFP sequence for E. coli expression as tetramers cctctcccagcaacccacgatttacacatctccggctcaatcaatggacatgagtttgacttggaaggcagtggcaagggcaatgcaaaag
aaggttatcaggagctccacctaaagtccaacaagggtgacctgtcattctcccccctggatTctggtcccaaacatcggctacggcttctac
cagtacctgcccttccccgacggagcgatgtcgccttaccaggccgccatgcacgatggctccggatacgtgatgcatcgttcaatgcagtt
tgaggatggtgccatgctgcattcagaccaccgctacatctataagggaaaccatatcaaaggagagtttcggctgaccggaagcggtttcc
ctgctgacggccctgtgatgaccaactcgctgaccgctgcggactggtgcgtcgacaagctgctgtacccaaacgacaacaccataatcg
gcaaaattcgactggacctacaccactaccagtggcaagcgctaccaaagtgatgtgcagaccaacgtcacatttggcaagccaatagcgg
ccgacattttgaagaagcagccaatgttcgtgttccgcaaggtggaactcaagcacaccaagactgagctcaacttcaagcagtggcagaa
ggcattccaggacatcgccggcatggacgagctgtacaagtaattaatgcag

FIG. 9A:

SEQ ID NO. 11: Translation of SEQ ID No 1. LanYFP sequence for E. coli expression as tetramers:

SLPATHELHIFGSFNGVDFDMVGRGTGNPNDGYEELNLKSTKGALQFSPWILVPQIGYG
FHQYLPFPDGMSPFQAAMKDGSGYQVHRTMQFEDGASLTSNYRYTYEGSHIKGEFQVI
GTGFPADGPVMTNSLTAADWCVTKMLYPNDKTIISTFDWTYTTGSGKRYQSTVRTNYT
FAKPMAANILKNQPMFVFRKTELKHSKTELNFKEWQKAFTDVMGMDELYK

FIG. 9B:

SEQ ID No. 12: Translation of SEQ ID No 2. LanRFP sequence for E. coli expression as tetramers:

PLPATHDLHISGSINGHEFDLEGSGKGNAKEGYQELHLKSNKGDLSFSPWILVPNIGYGF
YQYLPFPDGAMSPYQAAMHDGSGYVMHRSMQFEDGAMLHSDHRYIYKGNHIKGEFRL
TGSGFPADGPVMTNSLTAADWCVDKLLYPNDNTIIGKFDWTYTTTSGKRYQSDVQTNV
TFGKPIAADILKKQPMFVFRKVELKHTKTELNFKQWQKAFQDIAGMDELYK

LIGHT-ABSORBING COMPOSITIONS AND METHODS OF USE

RELATED APPLICATION

This application is a continuation-in-part of U.S. Ser. No. 14/961,678, filed on Dec. 7, 2015, which is a continuation-in-part application of U.S. Ser. No. 13/206,420, filed on Aug. 9, 2011 now U.S. Pat. No. 9,205,284, which claims the benefit of priority to U.S. provisional application Ser. No. 61/371,741, filed on Aug. 9, 2010, the contents of both which are incorporated by reference in their entirety.

SEQUENCE LISTING

The instant application contains a Sequence Listing which has been filed electronically in ASCII format and is hereby incorporated by reference in its entirety. Said ASCII copy, created on Nov. 15, 2018, is named F6035-00079_SL.txt and is 27,676 bytes in size.

FIELD OF THE INVENTION

The present disclosure relates to novel compositions and methods relating to the use of naturally occurring light-energy absorbing biological agents for dermatological and cosmeceutical applications. More specifically, certain aspects of this disclosure relate to light absorbing polypeptide formulations for topical cosmetic and/or dermatological applications.

BACKGROUND

Skin cancer is the most common type of cancer in the US and the vast majority of mutations found in melanoma are caused by UV radiation. Sun exposure is a well-known causal agent for many other skin-related conditions, such as melanoma, basal cell carcinoma, squamous cell carcinoma, photoaging, as well as sunburn. In addition to UVB or UVA, extensive exposure to lights in the visible range may also result in DNA damage. Light-energy induced damage can also result from exposure to other light sources such as industrial work lights, stage lights, tanning lights, etc. Various dermal layers of the skin are the primary sites of UV damage, however, other tissues can also be adversely affected by exposure to light, such as tissues of the eye, cells beneath the epidermis, and gum. Currently, commercially available sunscreens are primarily based on physical sun-blocking agents, which can include zinc oxide, titanium dioxide, and chemical UV (ultraviolet lights) absorbers/filters, such as octinoxate for UVB and benzophenone for UVA. Currently, existing UV absorbers/filters are formulated with chemicals that absorb UV lights within a very limited range of wavelength. Consequently, a combination of different chemicals are needed to achieve "broad-spectrum" UV protection. In addition, most of the sunscreen products on the markets today do not absorb UVA rays well enough to efficiently prevent against skin cancer. Furthermore, many of these commonly used chemicals suffer from lack of photostability as many agents lose their ability to absorb UV lights within a very short period of time (e.g. minutes) and thus drastically reducing their effectiveness.

SUMMARY OF THE INVENTION

Accordingly, in view of the problems associated with the previously known compositions, improved methods and compositions comprising naturally occurring light absorbing agents useful for topical cosmetic and/or dermatological applications are desired.

The present disclosure relates to the surprising and unexpected discovery that naturally occurring light absorbing proteins from *Brachiostoma* have surprising and unexpected efficacy in protecting against light damage.

In one aspect, a method is provided for protecting the state of the skin from light damage in a subject in need thereof, in which said method comprises topically administering a composition comprising a dermatologically acceptable carrier or a vehicle and a functional *Brachiostoma* light absorbing protein polypeptide derived from SEQ ID No: 11 formulated for topical administration and further comprising the following individual amino acid residues: Glu45, Trp61, Pro65, Gly68, Tyr69, Gly70, Phe71, His72, Tyr112, Trp167, Tyr169, Arg205, and Glu220 to yield SEQ ID NO: 13, as set forth below:

```
SEQ ID NO: 13 - Amino Acid Sequence
Ser Leu Pro Ala Thr His Glu Leu His Ile Phe Gly Ser
Phe Asn Gly Val Asp Phe Asp Met Val Gly Arg Gly Thr
Gly Asn Pro Asn Asp Gly Tyr Glu Glu Leu Asn Leu Lys
Ser Thr Lys Gly Ala Glu Gln Phe Ser Pro Trp Ile Leu
Val Pro Gln Ile Gly Tyr Gly Phe Trp Gln Tyr Leu Pro
Phe Pro Gly Tyr Gly Phe His Phe Gln Ala Ala Met Lys
Asp Gly Ser Gly Tyr Gln Val His Arg Thr Met Gln Phe
Glu Asp Gly Ala Ser Leu Thr Ser Asn Tyr Arg Tyr Thr
Tyr Glu Gly Ser His Ile Lys Tyr Glu Phe Gln Val Ile
Gly Thr Gly Phe Pro Ala Asp Gly Pro Val Met Thr Asn
Ser Leu Thr Ala Ala Asp Trp Cys Val Thr Lys Met Leu
Tyr Pro Asn Asp Lys Thr Ile Ile Ser Thr Phe Asp Trp
Thr Tyr Thr Thr Gly Ser Gly Lys Arg Tyr Trp Ser Tyr
Val Arg Thr Asn Tyr Thr Phe Ala Lys Pro Met Ala Ala
Asn Ile Leu Lys Asn Gln Pro Met Phe Val Phe Arg Lys
Thr Glu Leu Lys His Ser Lys Thr Glu Arg Asn Phe Lys
Glu Trp Gln Lys Ala Phe Thr Asp Val Met Gly Glu Asp
Glu Leu Tyr Lys
```

In another aspect, a method is provided for protecting the state of the skin from light damage in a subject in need thereof, in which said method comprises topically administering a composition comprising a dermatologically acceptable carrier or a vehicle and a functional *Brachiostoma* light absorbing protein polypeptide derived from SEQ ID No: 12 formulated for topical administration further comprising the following individual amino acid residue: Gln45, Trp61, Pro65, Gly68, Tyr69, Gly70, Phe71, Tyr72, His113, Asp152, Trp168, Tyr170, Arg206, and Gln221 to yield SEQ ID NO: 14, as set forth below:

```
SEQ ID NO: 14 - Amino Acid Sequence
Pro Leu Pro Ala Thr His Asp Leu His Ile Ser Gly Ser
Ile Asn Gly His Glu Phe Asp Leu Glu Gly Ser Gly Lys
```

-continued

```
Gly Asn Ala Lys Glu Gly Tyr Gln Glu Leu His Leu Lys

Ser Asn Lys Gly Asp Gln Ser Phe Ser Pro Trp Ile Leu

Val Pro Asn Ile Gly Tyr Gly Phe Trp Gln Tyr Leu Pro

Phe Pro Gly Tyr Gly Phe Tyr Pro Tyr Gln Ala Ala Met

His Asp Gly Ser Gly Tyr Val Met His Arg Ser Met Gln

Phe Glu Asp Gly Ala Met Leu His Ser Asp His Arg Tyr

Ile Tyr Lys Gly Asn His Ile Lys His Glu Phe Arg Leu

Thr Gly Ser Gly Phe Pro Ala Asp Gly Pro Val Met Thr

Asn Ser Leu Thr Ala Ala Asp Trp Cys Val Asp Lys Leu

Leu Tyr Pro Asn Asp Asn Thr Ile Asp Gly Lys Phe Asp

Trp Thr Tyr Thr Thr Thr Ser Gly Lys Arg Tyr Trp Ser

Tyr Val Gln Thr Asn Val Thr Phe Gly Lys Pro Ile Ala

Ala Asp Ile Leu Lys Lys Gln Pro Met Phe Val Phe Arg

Lys Val Glu Leu Lys His Thr Lys Thr Glu Arg Asn Phe

Lys Gln Trp Gln Lys Ala Phe Gln Asp Ile Ala Gly Gln

Asp Glu Leu Tyr Lys
```

In yet another aspect, a method is provided for protecting the state of the skin from light damage in a subject in need thereof, in which said method comprises topically administering a composition comprising a dermatologically acceptable carrier or a vehicle and a functional *Brachiostoma* light absorbing protein polypeptide formulated for topical administration comprising the following individual amino acid residue: Glu45, Trp61, Pro65, Gly68, Tyr69, Gly70, Phe71, His72, Tyr112, Trp167, Tyr169, Arg205, Glu220 or Gln45, Trp61, Pro65, Gly68, Tyr69, Gly70, Phe71, Tyr72, His113, Asp152, Trp168, Tyr170, Arg206, Gln221. In certain embodiments, the *Brachiostoma* polypeptide is a derived from *Brachiostoma floridae* or *Brachiostoma lanceolatum*.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the stability of FPs at room temperature (RT) for 18 months. From left to right, cultures of DH5a *E. coli* expressing fluorescent proteins mTFP1, mWasabi, mTangerine, mCherry after 18 months of storage at room temperature.

FIG. 2 shows the production of the recombinant LanYFP and LanRFP. From left to right, mTFP1 as a control and two representatives of the LanFP family, LanYFP (yellow) and LanRFP (red), were expressed in DH5a *E. coli*, purified using Cobalt-agarose beads, and stocked in PBS buffers. Fluorescent color images are displayed in black and white herein.

FIG. 3 shows recombinant LanYFP and LanRFP are stable and remain tetrameric in SDS-PAGE gel. Ten microliters of mTFP1, LanYFP, or LanRFP (left to right) protein samples were boiled in 1× protein loading dye that contains SDS and DTT for 3 min and immediately loaded onto precast SDS-PAGE gel. The electrophoresis was carried out at 120 volts for about 1 hour, and the picture was taken under a blue LED light. The position of the mTFP1 band (Cyan color) is of a monomer (~26 kD); LanYFP (yellow) and LanRFP (red) of tetramer (~105 kD).

FIG. 4 shows the heteratetramers between LanYFP and LanRFP. From left to right: 1:1 ratio mixtures of mWasabi:LanYFP (RT), mWasabi:LanRFP (RT), LanYFP:LanRFP (RT), mWasabi:LanYFP (−80 C), mWasabi:LanRFP (−80 C), LanYFP:LanRFP (−80 C).

FIG. 5 shows efficacy of the fluorescent proteins in protecting cells from UV-damage. Approximately 5 microgram of bacterially produced fluorescent proteins mWasabi, LanYFP, LanRFP, or control protein BSA was added to wells within alternating columns; the wells contained 293-T derived human cells which were exposed to 254 nm UV light for 5 minutes at room temperature in the presence of absence of the added proteins. The pictures within this figure are arranged exactly as they were on the 96-well plate.

FIGS. 6A and 6B show the LanYFP (SEQ ID No. 1) (FIG. 6A) and LanRFP (SEQ ID No. 2) (FIG. 6B) sequence for *E. coli* expression as tetramers. The sequences begin with a cloning tag of 33 nucleotides.

FIGS. 7A and 7B show the amino acid translation of the LanYFP (SEQ ID No. 3) (FIG. 7A) and Lan RFP (SEQ ID No. 4) (FIG. 7B) sequence for *E. coli* expression as tetramers. The sequences begin with a cloning tag of 33 amino acid residues.

FIGS. 8A and 8B show the LanYFP (SEQ ID No. 9) (FIG. 8A) and LanRFP (SEQ ID No. 10) (FIG. 8B) sequence for *E. coli* expression as tetramers.

FIGS. 9A and 9B show the amino acid translation of the LanYFP (SEQ ID No. 11) (FIG. 9A) and Lan RFP (SEQ ID No. 12) (FIG. 9B) sequence for *E. coli* expression as tetramers.

DETAILED DESCRIPTION OF THE INVENTION

When describing the present invention, all terms not defined herein have their common meanings recognized in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention.

The present disclosure is directed to the use of proteins that absorb lights efficiently and extensively. An example of such proteins are fluorescent proteins (FPs), as well as other protein families sharing similar structural and functional properties relevant to light absorbing abilities. Originally discovered in jelly fish, later in corals and other species, FPs have been used in scientific research extensively. FPs convert photons to harmless fluorescent lights, and in some cases scavenge superoxide radicals [3][4], but their potential benefits when used on human have not been fully explored. For use as research tools, FPs are often produced by protein engineering methods in laboratories for more desired properties such as different absorbance/excitation and emission spectra, improved photostability, monomerization, derivation of new FPs based on consensus sequences from a group of known FPs [5]. All isolated fluorescent proteins or engineered and recombinant FPs are contemplated for use in the embodiments in the instant disclosure because they absorb lights efficiently within a particular spectrum.

In view of the need of more efficient and broader-spectrum light protection (i.e. protection against damages caused by UVB, UVA, visible lights) products for health and cosmetic purposes, the embodiments of the current disclosure are extremely useful for absorbing damaging lights and free radicals, enhancing popular use of sunscreen products, and helping to improve the general health of the public.

Recently, multiple FPs were found within a single species, Amphioxus or lancelet, an animal that lives in sand on ocean beaches [6, 7]. A single lancelet genome encodes more than a dozen different FPs covering broad absorbance and emission spectra. These proteins display a wide spectrum of absorbance and show diverse abilities to quench light or to fluorescence. These proteins are extremely stable, maintaining intact structures and fluorescence capabilities in denaturing organic chemicals such as methanol or chloroform, after months of storage at elevated temperatures, or even during electrophoresis in SDS PAGE. In freezing conditions, interestingly, some of the lancelet FPs may remain in a phase separate from water. The current invention designed a novel light damage prevention product that contains the FPs from amphioxuses. For skin protection, the family of lancelet FPs (hereby referred to as LanFPs, with LanYFP for yellow lancelet FP, and LanRFP for red lancelet FP, etc.), is particularly suitable because sunscreen/sunblocker products often contain alcohol (for example, 79.6% V/V, SD Alcohol 40, in Coppertone Sport Sunblock Spray SPF 30) or other denaturing components that may denature native structures of proteins. Furthermore, products against sunray exposure are often used and applied at elevated temperature, under which other light-absorbing proteins may not be stored for long period of time in the product container or after being applied to skin. The functions of naturally existing LanFPs have not been known or scientifically analyzed. The current invention describes previously unknown and untested utilities of these proteins or proteins that share similar properties regardless of their potential functions when they exist in their natural states. Combined with the extraordinary stability and ease for production, LanFPs provide superior and revolutionizing light damage prevention products. Particularly, the current invention explores the benefit of using isolated LanFPs for skin protection.

In one aspect, similar to the use of LanFPs, the current disclosure provides a method of using light absorbing molecules produced by various living organisms (hereby referred to as biological products) that may be of various classes of molecules. Such molecules may include Chlorophylls and carotenoids, which are important in light-harvesting complexes present in plants. Light absorbing molecules may also include a phycobilisome, which is a light-harvesting protein complex present in cyanobacteria, glaucocystophyta, and red algae. The pigments phycocyanobilin and phycoerythrobilin that are present in the phycobilisome enhance the amount and spectral window of light absorption. The geometrical arrangement of a phycobilisome is very elegant and results in 95% efficiency of energy transfer. Allophycocyanin, which sits above a photosynthetic reaction center, and phycocyanin and phycoerythrin subunits that radiate out from this center like thin tubes, form an efficient core for light energy transfer. Some of these molecules have been used as fluorescent color dyes, but they have not been used in skin care products before the current invention. The use of the above mentioned molecules and the members of the groups of molecules with comparable properties for the disclosed utilities is hereby incorporated by reference.

In another aspect, other molecules that are produced by living organisms such as flavin mononucleotide (FMN), or riboflavin-5-phosphate, its various forms semiquinone (FMNH•) and reduced (FMNH2), flavin adenine dinucleotide (FAD), Nicotinamide adenine dinucleotide, abbreviated NAD+, etc. which may absorb photons and electrons effectively, are used for protection against light-caused damage in a similar manner as LanFPs as disclosed in the current invention. These chemicals can be used as reagents for light absorbance for the purpose of reducing the damage caused by light exposure. The use of the above mentioned molecules and other members of same groups of molecules in the invented products is hereby incorporated by reference.

In yet another aspect, the molecules incorporated into the compositions of light damage prevention products in the current invention also include phototropins, which function by binding light-absorbing chromophores to convert the energy of photons into structural and dynamical changes. Even though many molecules, including virtually all proteins, can absorb lights with damaging effects such as UV280, for use as reasonably effective components in commercial skincare products with anti-damaging benefits, this invention relies more on those with extraordinary abilities to absorb lights than ordinary proteins, DNAs, RNAs, or small molecules.

The term "complementary," as used herein, means that two nucleic acids, e.g., DNA or RNA, contain a series of consecutive nucleotides which are capable of forming matched Watson-Crick base pairs to produce a region of double-strandedness. Thus, adenine in one strand of DNA or RNA pairs with thymine in an opposing complementary DNA strand or with uracil in an opposing complementary RNA strand.

As used herein, homology and homologues sequences (eg. the polynucleotides or polypeptides may be a homologue of sequence) typically have at least 70% homology, preferably at least 80, 90%, 95%, 97% or 99% homology with the relevant sequence, for example over a region of at least 15, 20, 40, 100 more contiguous nucleotides of the homologous polynucleotide sequence or 5, 10, 15, 20, 40, 100 more continuous amino acids of the homologous polypeptide sequence.

Homology may be calculated based on any method in the art. For example, the UWGCG Package provides the BESTFIT program which can be used to calculate homology (for example used on its default settings) (Devereux et al (1984) Nucleic Acids Research 12, p 387-395). The PILEUP and BLAST algorithms can be used to calculate homology or line up sequences (typically on their default settings), for example as described in Altschul S. F. (1993) J Mol Evol 36: 290-300; Altschul, S, F et al (1990) J Mol Biol 215: 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than 0.001.

The homologous sequence typically differs from the relevant sequence by at least (or by no more than) 2, 5, 10, 15, 20 more mutations (which may be substitutions, deletions or insertions). These mutations may be measured across any of the regions mentioned above in relation to calculating homology.

The homologous polynucleotide sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook et al (1989), Molecular Cloning: A Laboratory Manual). For example, if high stringency is required, suitable conditions include 0.2×SSC at 60° C. If lower stringency is required, suitable conditions include 2×SSC at 60° C.

Those skilled in the art will recognize that the disclosure is also useful for the disclosure generally relates to novel methods and compositions relating to fluorescent proteins. As used herein, "fluorescent protein" refers to any protein with chromophore structure capable of absorbing light (light absorbing protein) or other electromagnetic radiation and emitting light in different wavelengths other than the exciting wave. A fluorescent protein referred to herein can also be a quencher, i.e. absorbing light without emitting a detectable light. Fluorescent proteins include proteins having amino acid sequences that are either natural or engineered, such as the fluorescent proteins derived from *Brachiostoma*-related fluorescent proteins.

According to a first aspect, the present disclosure is directed to a topical dermatological use of at least one peptide having the SEQ ID No 11 or SEQ ID No 12, and derivatives thereof.

As used herein, "peptide" and "polypeptide" refer to peptides which can contain only genetically encoded amino acids, only not genetically encoded amino acids, or a combination of genetically encoded and not genetically encoded amino acids. As used herein, the term "peptide" includes oligopeptide, peptide, polypeptide and derivatives thereof, peptide analogs and derivatives thereof, as well as dermatologically acceptable salts of these compounds. "Peptide analog" means synthetically modified amino acids or peptide, or a peptidic chain whose sequence presents homologies with the sequence of the similar reference peptide, in other words in which 1 or several amino acids were replaced by one or some other amino acids. As used herein, "peptides" encompass also complexes with other species such as metal ions (e.g., copper, zinc, manganese, magnesium, and the like).

The term "amino acid" as employed herein includes and encompasses all of the genetically encoded occurring, and non genetically encoded amino acids, either in the D- or L-configuration if optically active.

Peptidic sequences are indicated herein using a traditional three letter convention from left (N-terminal end) to right (C-terminal end). In this nomenclature, -Ala is Alanine, -Asn is Asparagine, -Cys is Cysteine, -Gln is Glutamine, -Gly is Glycine, -Ile is Isoleucine, -Leu is Leucine, -Met is Methionine, -Phe is Phenylalanine, or its analogs, particularly a halogenated derivative, more particularly parafluoro-Phe, Homo-Phe, para-nitroPhe or phenylglycine, -Pro is Proline, -Ser is Serine, -Thr is Threonine, -Trp is Tryptophan, -Tyr is Tyrosine, -Val is Valine, -Asp is Aspartic Acid, -Glu is Glutamic Acid, -Arg, is Arginine, -His is 'Histidine, -Lys is Lysine, -Orn is Ornithine, -Tic, is 1,2,3,4-tetrahydroisoquinoline-3-carboxylic acid (or tetrahydroisoquinoline-3-carboxylic acid), -7-OH-Tic is 7-hydroxy-1,2,3,4-tetrahydroisoquinoline-3-carboxylic acid, -Tpi is 1,2,3,4-tetrahydro-9H-pyrido[3,4-b]indole-3-carboxylic acid (or tryptoline-3-carboxylic acid).

In order to enhance the bioavailability and cutaneous barrier crossing of those peptides, their lipophilicity or lipophilic character can be increased either by acylation of the N-terminal NH2 group of the peptide, by esterification of the carboxyl group with an alcohol, linear or branched, saturated or unsaturated, hydroxylated or not, or both.

In another preferred embodiment, the said acyl group is bound to the N-terminal end of at least one amino acid and is a straight-chain or branched-chain, long or short chain, saturated or unsaturated, substituted with one or more hydroxyl, amino, acyl amino, sulfate or sulfide groups or may be unsubstituted, and which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidic acid, 2-ethylhexanoic acid, coconut oil fatty acid, tallow fatty acid, hardened tallow fatty acid, palm kernel oil fatty acid, lanolin fatty acid, biotinic acid, folic acid, decanoic acid, retinoic acid, sorbic acid, caproic acid, undecanoic acid, nicotinic acid, azelaic acid, propionic acid, butyric acid, valeric acid, lactic acid, malic acid or mixtures thereof.

The polypeptides of the present disclosure can be obtained by chemical or enzymatic synthesis from the constitutive amino acids or of their derivatives; or is obtained by mild hydrolysis of natural proteins; or by biotechnology, or by vegetal extraction.

The polypeptides of the present disclosure can be obtained by cloning, in which case SEQ ID NO. 1 and SEQ ID NO. 2 include 33 nucleotides which code for a cloning tag preceding the wild-type *Brachiostoma* sequence. SEQ ID NO. 3 and SEQ ID NO. 4 are translations of SEQ ID NO. 1 and SEQ ID NO. 2, respectively. SEQ ID NO. 9 is the Lan YFP sequence for *E. coli* expression as tetramers, without the cloning tag. SEQ ID NO. 10 is the Lan RFP sequence for *E. coli* expression as tetramers, without the cloning tag. SEQ ID NO. 11 is the translation of the Lan YFP sequence for *E. coli* expression as tetramers, without the cloning tag. SEQ ID NO. 12 is the translation of the Lan RFP sequence for *E. coli* expression as tetramers, without the cloning tag.

| Amino Acid Sequence |
|---|

Amino Acid Sequence
SEQ ID No. 3

Cloning Tag
[MVSKGEEDNMA]SLPATHELHIFGSFNGVDFDMVGRGTGNPDGYEELNLKSTKGALQFS

PWILVPQIGYGFHQYLPFPDGMSPFQAAMKDGSGYQVHRTMQFEDGASLTSNYRYTYE

GSHIKGEFQVIGTGFPADGPVMTNSLTAADWCVKMLYPNDKTIISTFDWTYTTGSGKRY

QSTVRTNYTFAKPMAANILKNQPMFVFRKTELKHSKTELNFKEWQKAFTDVMGMDEL

YK

Amino Acid Sequence
SEQ ID NO. 4

Cloning Tag
[MVSKGEEDNMA]PLPATHDLHISGSINGHEFDLEGSGKGNAKEGYQELHLKSNKGDLSFS

PWILVPNIGYGFYQULPFPDGAMSPYQAAMHDGSGYVMHRSMQFEDGAMLHSDHRYI

YKGNHIKGEFRLTGSGFPADGPVMTNSLTAADWCVDKLLYPNDNTIIGKFDWTYTTTSG

KRYQSDVQTNVTFGKPIAADILKKQPMFVFRKVELKHTKTELNFKQWQKAFQDIAGMD

ELYK

The present disclosure relates also to a cosmetic or dermopharmaceutical composition comprising a safe and effective amount of at least one compound having SEQ ID No. 11 or 12 and a dermatologically acceptable carrier.

Peptides used in cosmetic and dermopharmaceutical compositions can be used at concentration which may range from, for example, 0.00001% (w/w) to 100% (w/w), between 0.0001% (w/w) and 20% (w/w) or between 0.001% and 5% (w/w) by weight of the composition.

The compositions of the present disclosure can comprise or consist essentially of the components of the present disclosure as well as other ingredients described herein. As used herein, "consisting essentially of" means that the composition or component may include additional ingredients, but only if the additional ingredients do not materially alter the basic and novel characteristics of the claimed compositions or methods. Preferably, such additives will not be present at all or only in trace amounts.

The term "dermatologically acceptable", as used herein, means that the compositions or components described are suitable for use in contact with human skin without risk of toxicity, incompatibility, instability, allergic response, and the like.

All terms such as "skin aging", "signs of skin aging", "topical application", "skin whitening", "loss of pigmentation" and the like are used in the sense in which they are generally and widely used in the art of developing, testing and marketing cosmetic and personal care products. The term "cosmetic composition" or more briefly just "composition" in accordance with the present disclosure relates to a formulation that can be used for cosmetic purposes, purposes of hygiene or as a basis for delivery of one or more dermopharmaceutical ingredients. This includes cosmetics, personal care products and pharmaceutical preparations. It is also possible that these formulations are used for two or more of these same purposes at one time. A medicated dandruff shampoo, for example, has pharmacological properties and is used as a personal care product to provide clean hair.

"Signs of skin aging" and other phrases similarly referring to, for example, symptoms of aging and the like include, but are not limited to, all outward visibly and tactilely perceptible manifestations as well as any other macro or micro effects due to skin aging. Such signs may be induced or caused by intrinsic factors and/or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinisation, elastosis, collagen breakdown and other histological changes in the stratum corneum, dermis, epidermis, the skin vascular system (e.g., telangiectasia or spider vessels), and underlying tissues, especially those proximate to the skin. As used herein, the term "visible and/or tactile discontinuities in skin" may encompass the stretch marks.

The composition according to the present disclosure has the aim of decreasing pigmentation, in particular to lighten the complexion, attenuate senile lentigo, or homogenize skin color. In other words, the present disclosure relates to cosmetic and dermatological composition for the prophylaxis and treatment of cosmetic or dermatological changes in skin, such as, for example, undesired pigmentation, for example local hyperpigmentation and incorrect pigmentation, the inhibition of natural pigmentation, or for the purely cosmetic lightening of relatively large areas of skin which are quite appropriately pigmented for the individual skin type.

In certain aspects, the composition according to the present disclosure useful as whitening and pigmentation reducing agent, preferably for the topical treatment of the human skin, preferably for effectively reducing skin problems caused by pigmentation such as liver spots, freckles and dark complexion, is also used for improving the physiological state and/or the physical appearance of human skin, in particular to reduce, prevent or treat the signs of skin aging that are generated by sun exposure, physical and hormonal stress, abrasion, nutritional effects and other similar causes.

Some of the compositions of the present disclosure may also provide additional benefits, including stability, absence of significant (consumer-unacceptable) skin irritation, anti-inflammatory activity and good aesthetics.

In a particular embodiment, the composition of the present disclosure contains further one or more one skin care active or additional ingredient selected from the group comprising: skin depigmenting agent, skin whitening agent, lightening or bleaching agent, optical brightening agent, melanogenesis inhibitor agent, reducing pigmentation agent, keratolytic agent, desquamation agent, skin anti-aging agent, anti-wrinkle agent, anti-atrophy agent, anti-oxidant/radical scavenger and mixtures thereof. Examples of said skin care active or additional ingredient are, without limitation: tyrosinase inhibitor, protein kinase A or C inhibitor, inhibitor of cellular calcium flux, inhibitor of adrenergic receptors α or β, hydroquinone, arbutin, kojic acid and its derivatives, vitamin C, vitamin E, vitamin A and their derivatives, boldine and its derivatives, licorice extract, citrus extract, bearberry extract, orange extract, lemon extract, cucumber extract, mulberry extract, rosemary extract, hops extract, mercaptosuccinic acid, mercaptodextran, glutathione, cysteine and its derivatives such as N-acetyl-L-cysteine, tocopherols, retinol, retinoic acid and retinaldehyde and mixtures.

"Adjuvants", "additives", and "optional components" are used synonymously with "additional ingredients". "Skin care actives", "actives" are used synonymously with "actives ingredients".

Additives

According to the present disclosure, the dermatologically acceptable carrier can be an aqueous or hydroalcoholic solution, a water in oil emulsion, an oil in water emulsion, a microemulsion, an aqueous gel, an anhydrous gel, a serum or a vesicle dispersion.

The compositions of the present disclosure may include various other and additional ingredients, which may be active, functional, conventionally used in cosmetic, personal care or topical/transdermal pharmaceutical products or otherwise. Of course, a decision to include an additional ingredient and the choice of specific additional ingredients depends on the specific application and product formulation. Also, the line of demarcation between an "active" ingredient and an "inactive ingredient" is artificial and dependent on the specific application and product type. A substance that is an "active" ingredient in one application or product may be a "functional" ingredient in another, and vice versa.

Thus, the compositions of the present disclosure may include at least one skin care active. As used herein, "skin care actives" are additional ingredients, which provide some benefit to the object of the composition. Such additional ingredients may include one or more substances such as, without limitations, cleaning agents, hair conditioning agents, skin conditioning agents, hair styling agents, anti-dandruff agents, hair growth promoters, perfumes, sunscreen and/or sunblock compounds, pigments, moisturizers, film formers, hair colors, make-up agents, detergents, pharmaceuticals, thickening agents, emulsifiers, humectants, emollients, antiseptic agents, deodorant actives, dermatologically acceptable carriers and surfactants.

In any embodiment of the present disclosure, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

In a preferred embodiment, where the composition is to be in contact with human keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment.

The CTFA Cosmetic Ingredient Handbook, Tenth Edition (published by the Cosmetic, Toiletry, and Fragrance Association, Inc., Washington, D.C.) (2004) describes a wide variety of nonlimiting materials that can be added to the composition herein. Examples of actives which may be added, include, but are not limited to: skin soothing and healing agents, skin anti-aging agents, skin moisturizing agents, anti-wrinkle agents, anti-atrophy agents, skin smoothing agents, antibacterial agents, antifungal agents, pesticides, anti parasitic agents, antimicrobial agents, anti-inflammatory agents, anti-pruriginous agents, external anaesthetic agents, antiviral agents, keratolytic agents, free radicals scavengers, antiseborrheic agents, antidandruff agents, the agents modulating the differentiation, proliferation or pigmentation of the skin and agents accelerating penetration, desquamating agents, depigmenting or propigmenting agents, antiglycation agents, tightening agents, agents stimulating the synthesis of dermal or epidermal macromolecules and/or preventing their degradation; agents stimulating the proliferation of fibroblasts and/or keratinocytes or stimulating the differentiation of keratinocytes; muscle relaxants; antipollution and/or anti-free radical agents; slimming agents, anticellulite agents, agents acting on the microcirculation; agents acting on the energy metabolism of the cells; cleaning agents, hair conditioning agents, hair styling agents, hair growth promoters, sunscreen and/or sunblock compounds, make-up agents, detergents, pharmaceutical drugs, emulsifiers, emollients, antiseptic agents, deodorant actives, dermatologically acceptable carriers, surfactants, abrasives, absorbents, aesthetic components such as fragrances, colorings/colorants, essential oils, skin sensates, cosmetic astringents, anti-acne agents, anti-caking agents, anti foaming agents, antioxidants, binders, biological additives, enzymes, enzymatic inhibitors, enzyme-inducing agents, coenzymes, plant extracts, plant derivatives, plant tissue extracts, plant seed extracts, plant oils, botanicals, botanical extracts, ceramides, peptides, buffering agents, bulking agents, chelating agents, chemical additives, colorants, cosmetic biocides, denaturants, drug astringents, external analgesics, film formers or materials, e.g., polymers, for aiding the film-forming properties and substantivity of the composition, quaternary derivatives, agents increasing the substantivity, opacifying agents, pH adjusters, pH regulator (e.g. triethanolamine), propellants, reducing agents, sequestrants, skin bleaching and lightening agents, skin tanning agents, skin-conditioning agents (e.g., humectants, including miscellaneous and occlusive), skin soothing and/or healing agents and derivatives, skin treating agents, thickeners, lipid thickener (e.g. stearic acid), vitamins and derivatives thereof, peeling agents, moisturizing agents, curative agents, lignans, preservatives (e.g. phoxyethanol and parabens), UV absorbers, a cytotoxic, an anti-neoplastic agent, a fat-soluble active, suspending agents, viscosity modifiers, dyes, non-volatile solvents, diluents, pearlescent aids, foam boosters, a vaccine, a water-soluble sunscreen, antiperspirant, depilatory, perfumed water, fat soluble sunscreens substance intended to improve the state of dry or aged skin, skin restructuring agent (e.g. *Siegesbeckia orientalis* extract), emollient (e.g. C12-15 alkyl benzoate), excipients, fillers, minerals, anti-mycobacterial agents, anti-allergenic agents, H1 or H2 antihistamines, anti-irritants, immune system boosting agents, immune system suppressing agents, insect repellents, lubricants, staining agents, hypopigmenting agents, preservatives, photostabilizing agents and their mixture.

Said additional ingredient is selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, peptides and their derivatives, di-, tri-, tetra-, penta-, and hexapeptides and their derivatives, lys-thr-thr-lys-ser (SEQ ID NO: 5), palmitoyl-lys-thr-thr-lys-ser (SEQ ID NO: 6), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins their salts and derivatives, provitamins and their salts and derivatives, ethyl panthenol, vitamin B, vitamin B derivatives, vitamin B1, vitamin B2, vitamin B6, vitamin B12, vitamin K, vitamin K derivatives, pantothenic acid and its derivatives, pantothenyl ethyl ether, panthenol and its derivatives, dexpanthenol, ethyl panthenol, biotin, amino acids and their salts and derivatives, water soluble amino acids, asparagine, alanine, indole, glutamic acid, water insoluble vitamins, vitamin A, vitamin E, vitamin F, vitamin D, mono-, di-, and tri-terpenoids, beta-ionol, cedrol, and their derivatives, water insoluble amino acids, tyrosine, tryptamine, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, other natural peptides, soy peptides, salts of sugar acids, Mn gluconate, Zn gluconate, particulate materials, pigment materials, natural colors, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and its salts, dihydroxyacetone, erythrulose, glyceraldehyde, tartaraldehyde, clove oil, menthol, camphor, eucalyptus oil, eugenol, menthyl lactate, witch hazel distillate, eicosene and vinyl pyrrolidone copolymers, iodopropyl butylcarbamate, a polysaccharide, an essential fatty acid, salicylate, glycyrrhetinic acid, carotenoïdes, ceramides and pseudo-ceramides, a lipid complex, oils in general of natural origin such Shea butter, apricot oil, onagre oil, prunus oil, palm oil, monoi oil, HEPES; procysteine; 0-octanoyl-6-D-maltose; the disodium salt of methylglycinediacetic acid, steroids such as diosgenin and derivatives of DHEA; N-ethyloxycarbonyl-4-para-aminophenol, bilberry extracts; phytohormones; extracts of the yeast *Saccharomyces cerevisiae*; extracts of algae; extracts of soybean, lupin, maize and/or pea; alverine and its salts, in particular alverine citrate, extract of butcher's broom and of horse chestnut, and mixtures thereof, without this list being limiting.

In any embodiment of the present disclosure, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

Sugar Amines (Amino Sugars)

The compositions of the present disclosure can comprise a sugar amine, which is also known as amino sugar. Sugar amine compounds useful in the present disclosure can include those described in PCT Publication WO 02/076423 and U.S. Pat. No. 6,159,485. In one embodiment, the composition comprises from about 0.01% to about 15%, more preferably from about 0.1% to about 10%, and even more preferably from about 0.5% to about 5% by weight of the composition, of sugar amine.

Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine.

Vitamin B3 Compounds

The compositions of the present disclosure can include a vitamin B3 compound. Vitamin B3 compounds are particularly useful for regulating skin conditions, as described in U.S. Pat. No. 5,939,082. In one embodiment, the composition comprises from about 0.001% to about 50%, more preferably from about 0.01% to about 20%, even more preferably from about 0.05% to about 10%, and still more preferably from about 0.1% to about 7%, even more preferably from about 0.5% to about 5%, by weight of the composition, of the vitamin B3 compound.

As used herein, "vitamin B3 compound" means a compound having the formula:

wherein R is —CONH2 (i.e., niacinamide), —COOH (i.e., nicotinic acid) or —CH2OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g, tocopherol nicotinate, myristyl nicotinate), nicotinyl amino acids, nicotinyl alcohol esters of carboxylic acids, nicotinic acid N-oxide and niacinamide N-oxide.

Suitable esters of nicotinic acid include nicotinic acid esters of C1-C22, preferably C1-C16, more preferably C1-C6 alcohols. Non-vasodilating esters of nicotinic acid include tocopherol nicotinate and inositol hexanicotinate; tocopherol nicotinate is preferred.

Other derivatives of the vitamin B3 compound are derivatives of niacinamide resulting from substitution of one or more hydrogens of the amide group. Specific examples of such derivatives include nicotinuric acid (C8H8N2O3) and nicotinyl hydroxamic acid (C6H6N2O2).

Exemplary nicotinyl alcohol esters include nicotinyl alcohol esters of the carboxylic acids salicylic acid, acetic acid, glycolic acid, palmitic acid and the like. Other non-limiting examples of vitamin B3 compounds useful herein are 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl)urea, 2-mercaptonicotinic acid, nicomol, and niaprazine.

Examples of the above vitamin B3 compounds are well known in the art and are commercially available from a number of sources, e.g., the Sigma Chemical Company; ICN Biomedicals, Inc. and Aldrich Chemical Company.

One or more vitamin B3 compounds may be used herein. Preferred vitamin B3 compounds are niacinamide and tocopherol nicotinate. Niacinamide is more preferred. When used, salts, derivatives, and salt derivatives of niacinamide are preferably those having substantially the same efficacy as niacinamide.

Salts of the vitamin B3 compound are also useful herein. Nonlimiting examples of salts of the vitamin B3 compound useful herein include organic or inorganic salts, such as inorganic salts with anionic inorganic species (e.g., chloride, bromide, iodide, carbonate, preferably chloride), and organic carboxylic acid salts (including mono-, di- and tri-C1-C18 carboxylic acid salts, e.g., acetate, salicylate, glycolate, lactate, malate, citrate, preferably monocarboxylic acid salts such as acetate). These and other salts of the vitamin B3 compound can be readily prepared by the skilled artisan (<<The Reaction of L-Ascorbic and D-Iosascorbic Acid with Nicotinic Acid and Its Amide", J. Organic Chemistry, Vol. 14, 22-26 (1949)).

The vitamin B3 compound may be included as the substantially pure material, or as an extract obtained by suitable physical and/or chemical isolation from natural (e.g., plant) sources. The vitamin B3 compound is preferably substantially pure, more preferably essentially pure.

Dehydroacetic Acid (DHA)

The composition of this present disclosure can include dehydroacetic acid, having the structure:

or pharmaceutically acceptable salts, derivatives or tautomers thereof. The technical name for dehydroacetic acid is 3-Acetyl-6-methyl-2H-pyran-2,4(3H)-dione and can be commercially purchased from Lonza.

Pharmaceutically acceptable salts include alkali metal salts, such as sodium and potassium; alkaline earth metal salts, such as calcium and magnesium; non-toxic heavy metal salts; ammonium salts; and trialkylammonium salts, such as trimethylammonium and triethylammonium. Sodium, potassium, and ammonium salts of dehydroacetic acid are preferred. Highly preferred is sodium dehydroacetate which can be purchased from Tri-K, as Tristat SDHA. Derivatives of dehydroacetic acid include, but are not limited to, any compounds wherein the CH3 groups are individually or in combination replaced by amides, esters, amino groups, alkyls, and alcohol esters. Tautomers of dehydroacetic acid can be described as having the chemical formula C8H8O4 and generally having the structure above.

In one embodiment, the compositions of the present disclosure can comprise from about 0.001% to about 25% by weight of the composition, preferably from about 0.01% to about 10%, more preferably from about 0.05% to about 5%, and even more preferably from about 0.1% to about 1%, of dehydroacetic acid or pharmaceutically acceptable salts, derivatives or tautomers thereof.

Phytosterol

The compositions of the present disclosure can comprise a phytosterol. For example, one or more phytosterols can be selected from the group consisting of β-sitosterol, campesterol, brassicasterol, Δ5-avennasterol, lupenol, α-spinasterol, stigmasterol, their derivatives, analogs, and combinations thereof. More preferably, the phytosterol is selected from the group consisting of β-sitosterol, campesterol, brassicasterol, stigmasterol, their derivatives, and combinations thereof. More preferably, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company and Cognis.

In one embodiment, the composition of the present disclosure comprises from about 0.0001% to about 25%, more preferably from about 0.001% to about 15%, even more preferably from about 0.01% to about 10%, still more preferably from about 0.1% to about 5%, and even more preferably from about 0.2% to about 2% of phytosterol, by weight of the composition.

Salicylic Acid Compound

The compositions of the present disclosure may comprise a salicylic acid compound, its esters, its salts, or combinations thereof. In one embodiment of the compositions of the present disclosure, the composition preferably comprises from about 0.0001% to about 25%, more preferably from about 0.001% to about 15%, even more preferably from about 0.01% to about 10%, still more preferably from about 0.1% to about 5%, and even more preferably from about 0.2% to about 2%, by weight of the composition, of salicylic acid compound.

Hexamidine

The compositions of the present disclosure can include hexamidine compounds, its salts, and derivatives.

In one embodiment, the composition comprises from about 0.0001% to about 25%, more preferably from about 0.001% to about 10%, more preferably from about 0.01% to about 5%, and even more preferably from about 0.02% to about 2.5% of hexamidine by weight of the composition.

As used herein, hexamidine derivatives include any isomers and tautomers of hexamidine compounds including but not limited to organic acids and mineral acids, for example sulfonic acid, carboxylic acid, etc. Preferably, the hexamidine compounds include hexamidine diisethionate, commercially available as Eleastab® HP100 from Laboratoires Serobiologiques.

Dialkanoyl Hydroxyproline Compounds

The compositions of the present disclosure can comprise one or more dialkanoyl hydroxyproline compounds and their salts and derivatives.

In one embodiment, the dialkanoyl hydroxyproline compounds are preferably added to the composition from about 0.01% to about 10%, more preferably from about 0.1% to about 5%, even more preferably from about 0.1% to about 2% by weight of the composition Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline.

Flavonoids

The compositions of the present disclosure can comprise a flavonoid compound. Flavonoids are broadly disclosed in U.S. Pat. No. 5,686,082. As used herein, "flavonoid" means unsubstituted flavonoid or substituted flavonoid (i.e. mono-substituted flavonoid, or/and di-substituted flavonoid, or/and tri-substituted flavonoid). Examples of flavonoids particularly suitable for use in the present disclosure are one or more flavones, one or more flavanones, one or more isoflavones, one or more coumarins, one or more chromones, one or more dicoumarols, one or more chromanones, one or more chromanols, isomers (e.g., cis/trans isomers) thereof, and mixtures thereof.

Preferred for use herein are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Also preferred are favanones such as hesperitin, hesperidin, and mixtures thereof.

In one embodiment, the herein described flavonoid compounds may be added from about 0.01% to about 20%, more preferably from about 0.1% to about 10%, and even more preferably from about 0.5% to about 5%, by weight of the composition.

N-acyl Amino Acid Compound

The topical compositions of the present disclosure can comprise one or more N-acyl amino acid compounds. The amino acid can be one of any of the amino acids known in the art. The N-acyl amino acid compounds of the present disclosure can correspond to the formula:

wherein R can be a hydrogen, alkyl (substituted or unsubstituted, branched or straight chain), or a combination of alkyl and aromatic groups.

Preferably, the N-acyl amino acid compound is selected from the group comprising N-acyl Phenylalanine, N-acyl Tyrosine, their isomers, their salts, and derivatives thereof. The amino acid can be the D or L isomer or a mixture thereof.

Among the broad class of N-acyl Phenylalanine derivatives, particularly useful is N-undecylenoyl-L-phenylalanine commercially available under the tradename Sepiwhite® from SEPPIC.

In one embodiment, the present disclosure preferably comprises from about 0.0001% to about 25%, more preferably from about 0.001% to about 10%, more preferably from about 0.01% to about 5%, and even more preferably from about 0.02% to about 2.5% of the N-acyl amino acid by weight of the composition.

Retinoid

The compositions of this present disclosure can comprise a retinoid, preferably in a safe and effective amount such that the resultant composition is safe and effective for regulating keratinous tissue condition, preferably for regulating visible and/or tactile discontinuities in keratinous tissue (e.g., regulating signs of skin aging). The compositions can comprise from about 0.001% to about 10%, more preferably from about 0.005% to about 2%, even more preferably from about 0.01% to about 1%, still more preferably from about 0.01% to about 0.5%, by weight of the composition, of the retinoid. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid. These compounds are well known in the art and are commercially available from a number of sources, e.g., Sigma Chemical Company, and Boerhinger Mannheim. Other retinoids which are useful herein are described in U.S. Pat. Nos. 4,677,120, 4,885,311, 5,049,584, 5,124,356, and Reissue 34,075. Other suitable retinoids can include tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 642-(4,4-dimethylthio-chroman-6-yl)-ethynyl]nicotinate). Preferred retinoids include retinol, retinyl palmitate, retinyl acetate, retinyl propionate, retinal and combinations thereof. More preferred is retinyl propionate, used most preferably from about 0.1% to about 0.3%.

The retinoid may be included as the substantially pure material, or as an extract obtained by suitable physical and/or chemical isolation from natural (e.g., plant) sources. The retinoid is preferably substantially pure, more preferably essentially pure.

Optional Peptide

The composition of the present disclosure can comprise an additional peptide. Suitable peptides can include, but are not limited to, di-, tri-, tetra-, penta-, and hexa-peptides and derivatives thereof. In one embodiment, the composition comprises from about 1×10-7% to about 20%, more preferably from about 1×10-6% to about 10%, even more preferably from about 1×10-5% to about 5%, by weight of additional peptide.

As used herein, "additional peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

Ascorbates and Other Vitamins

The compositions of the present disclosure may comprise one or more vitamins, such as ascorbates (e.g., vitamin C, vitamin C derivatives, ascorbic acid, ascorbyl glucoside, ascorbyl palmitate, magnesium ascorbyl phosphate, sodium ascorbyl phosphate). Such vitamins can include, but are not limited to, vitamin B, vitamin B derivatives, vitamin B1 to vitamin B12 and their derivatives, vitamin K, vitamin K derivatives, vitamin H vitamin D, vitamin D derivatives, vitamin E, vitamin E derivatives, and provitamins thereof, such as panthenol and mixtures thereof. The vitamin compounds may be included as the substantially pure material, or as an extract obtained by suitable physical and/or chemical isolation from natural (e.g., plant) sources. In one embodiment, when vitamin compounds are present in the compositions of the instant present disclosure, the compositions comprise from about 0.0001% to about 50%, more preferably from about 0.001% to about 10%, still more preferably from about 0.01% to about 8%, and still more preferably from about 0.1% to about 5%, by weight of the composition, of the vitamin compound.

Particulate Material

The compositions of the present disclosure can comprise one or more particulate materials. Non limiting examples of particulate materials useful in the present disclosure include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein can include, but are not limited to, bismuth oxychloride, sericite, silica, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Preferred organic powders/fillers include, but are not limited, to polymeric particles chosen from the methylsilsesquioxane resin microspheres such as, for example, those sold by Toshiba silicone under the name Tospearl 145A, microspheres of polymethylmethacrylates such as those sold by Seppic under the name Micropearl M 100, the spherical particles of crosslinked polydimethylsiloxanes, especially such as those sold by Dow Corning Toray Silicone under the name Trefil E 506C or Trefil E 505C, spherical particles of polyamide and more specifically Nylon 12, especially such as those sold by Atochem under the name Orgasol 2002D Nat C05, polystyrene microspheres such as for example those sold by Dyno Particles under the name Dynospheres, ethylene acrylate copolymer sold by Kobo under the name FloBead EA209, PTFE, polypropylene, aluminium starch octenylsuccinate such as those sold by National Starch under the name Dry Flo, microspheres of polyethylene such as those sold by Equistar under the name of Microthene FN510-00, silicone resin, polymethylsilsesquioxane silicone polymer, platelet shaped powder made from L-lauroyl lysine, and mixtures thereof.

Also useful herein are interference pigments. The most common examples of interference pigments are micas layered with about 50-300 nm films of TiO2, Fe2O3, silica, tin oxide, and/or Cr2O3. Useful interference pigments are available commercially from a wide variety of suppliers, for example, Rona (Timiron™ and Dichrona™), Presperse (Flonac™) Englehard (Duochrome™), Kobo (SK-45-R and SK-45-G), BASF (Sicopearls) and Eckart (e.g. Prestige Silk Red).

Other pigments useful in the present disclosure can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present disclosure, for example TiO2, ZnO, or ZrO2, are commercially available from a number of sources. One example of a suitable particulate material contains the material available from U.S. Cosmetics (TRONOX TiO2 series, SAT-T CR837, a rutile TiO2), another example is OPTISOL, proposed by Oxonica.

The pigments/powders of the current present disclosure can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobic treatments being preferred.

Additional Sunscreen Actives

The compositions of the subject present disclosure may optionally contain another sunscreen active in combination. As used herein, "sunscreen active" includes both sunscreen agents and physical sunblocks. Suitable sunscreen actives may be organic or inorganic.

A wide variety of conventional organic or inorganic sunscreen actives are suitable for use herein. In one embodiment, the composition comprises from about 0.1% to about 20%, more typically from about 0.5% to about 10% by weight of the composition, of the sun screen active. Exact amounts will vary depending upon the sunscreen chosen and the desired Sun Protection Factor (SPF).

As examples of organic screening agents which are active in UV-A and/or UV-B, there may be mentioned in particular those designated below by their CTFA name: para-aminobenzoic acid derivatives: PABA, Ethyl PABA, Ethyl Dihydroxypropyl PABA, Ethylhexyl Dimethyl PABA sold in particular under the name "ESCALOL 507" by ISP, Glyceryl PABA, PEG-25 PABA sold under the name "UVINUL P25" by BASF, salicyclic derivatives: Homosalate sold under the name "EUSOLEX HMS" by RONA/EM INDUSTRIES, Ethylhexyl Salicylate sold under the name "NEO HELIOPAN OS" by HAARMANN and REIMER, Dipropyleneglycol Salicylate sold under the name "DIPSAL" by SCHER, TEA Salicylate, sold under the name "NEO HELIOPAN TS" by HAARMANN and REIMER, dibenzoylmethane derivatives: Butyl Methoxydibenzoylmethane sold in particular under the trademark "PARSOL 1789" by HOFFMANN LA ROCHE, Isopropyl Dibenzolylmethane, cinnamic derivatives: Ethylhexyl Methoxycinnamate sold in particular under the trademark "PARSOL MCX" by HOFFMANN LA ROCHE, Isopropyl Methoxy Cinnamate, Isoamyl Methoxy Cinnamate sold under the trademark "NEO HELIOPAN E 1000" by HAARMANN and REIMER, Cinoxate, DEA Methoxycinnamate, Diisopropyl Methylcinnamate, Glyceryl Ethylhexanoate Dimethoxycinnamate, β β'-diphenylacrylate derivatives: Octocrylene sold in particular under the trademark "UVINUL N539" by BASF, Etocrylene, sold in particular under the trademark "UVINUL N35" by BASF, benzophenone derivatives: Benzophenone-1 sold under the trademark "UVINUL 400" by BASF, Benzophenone-2 sold under the trademark "UVINUL D50" by BASF, Benzophenone-3 or Oxybenzone, sold under the trademark "UVINUL M40" by BASF, Benzophenone-4 sold under the trademark "UVINUL MS40" by BASF, Benzophenone-5, Benzophenone-6 sold under the trademark "HELISORB 11" by NORQUAY, Benzophenone-8 sold under the trademark "SPECTRA-SORB UV-24" by AMERICAN CYANAMID, Benzophenone-9 sold under the trademark "UVINUL DS-49" by BASF, Benzophenone-12, benzylidene camphor derivatives: 3-Benzylidene Camphor, 4-Methylbenzylidene Camphor sold under the name "EUSOLEX 6300" by MERCK, Benzylidene Camphor Sulphonic Acid, Camphor Benzalkonium Methosulphate, Terephthalylidene Dicamphor Sulphonic Acid, Polyacrylamidomethyl Benzylidene Camphor, phenylbenzimidazole derivatives: Phenylbenzimidazole Sulphonic Acid sold in particular under the trademark "EUSOLEX 232" by MERCK, Benzimidazilate sold under the trademark "NEO HELIOPAN AP" by HAARMANN and REIMER, triazine derivatives: Anisotriazine sold under the trademark "TINOSORB S" by CIBA GEIGY, Ethylhexyl triazones sold in particular under the trademark "UVINUL T150" by BASF, Diethylhexyl Butamido Triazone sold under the trademark "UVASORB HEB" by SIGMA 3V, phenylbenzotriazole derivatives: Drometrizole Trisiloxane sold under the name "SILATRIZOLE" by RHODIA CHIMIE, anthranilic derivatives: Menthyl anthranilate sold under the trademark "NEO HELIOPAN MA" by HAARMANN and REIMER, imidazoline derivatives: Ethylhexyl Dimethoxybenzylidene Dioxoimidazoline Propionate, benzalmalonate derivatives: Polyorganosiloxane with benzalmalonate functional groups sold under the trademark "PARSOL SLX" by HOFFMANN LA ROCHE, and mixtures thereof. others: dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); uric and violuric acids; tannic acid and its derivatives (e.g., hexaethylether); (butyl carbotol) (6-propyl piperonyl)ether; hydroquinone; The organic UV-screening agents which are more particularly preferred are chosen from the following compounds: Ethylhexyl Salicylate, Butyl Methoxydibenzoylmethane, Ethylhexyl Methoxycinnamate, Octocrylene, Phenylbenzimidazole Sulphonic Acid, Terephthalylidene Dicamphor Sulphonic, Benzophenone-3, Benzophenone-4, Benzophenone-5, 4-Methylbenzylidene camphor, Benzimidazilate, Anisotriazine, Ethylhexyl triazone, Diethylhexyl Butamido Triazone, Methylene bis-Benzotriazolyl Tetramethylbutylphenol, Drometrizole Trisiloxane, and mixtures thereof.

The inorganic screening agents which may be used in the composition according to the present disclosure are in particular nanopigments (mean size of the primary particles: generally, between 5 nm and 100 nm, preferably between 10 nm and 50 nm) of coated or uncoated metal oxides such as for example nanopigments of titanium oxide (amorphous or crystallized in the form of rutile and/or anatase), iron, zinc, zirconium or cerium oxides and mixtures thereof. Coating agents are moreover alumina and/or aluminum stearate. Such nanopigments of metal oxides, coated or uncoated, are in particular described in EP-A-0-518,772 and EP-A-0-518,773. One preferred TiO2/ZnO2 sunscreen agent is OPTISOL, proposed by Oxonica.

When used herein, the inorganic sunscreens are present in the amount of from about 0.1% to about 20%, preferably from about 0.5% to about 10%, more preferably from about 1% to about 5%, by weight of the composition.

Anti-Cellulite Agents

The compositions of the present disclosure may also comprise an anti-cellulite agent. Suitable agents may include, but are not limited to, xanthine compounds (e.g., caffeine, theophylline, theobromine, and aminophylline). In one embodiment, when anti-cellulite compounds are present in the compositions of the instant present disclosure, the compositions comprise from about 0.0001% to about 50%, more preferably from about 0.001% to about 10%, still more preferably from about 0.01% to about 8%, and still more preferably from about 0.1% to about 5%, by weight of the composition, of the anti-cellulite compound.

Slimming, Toning or Draining Actives

The compositions can include one or more lipolytic agent selected among: phosphodiesterase inhibitors (e.g., xanthine derivatives), alpha-2 blockers compounds capable of blocking alpha-2 receptors at the adipocytes surface, beta-adrenergical agonists and antagonists (e.g. alverine and its organic or inorganic salts such as alverine citrate), agents inhibiting LDL and VLDL receptors synthesis, inhibitors of enzymes of fatty acid synthesis such as acetylCoA carboxylase, or fatty acid synthetase or cerulenine, compounds stimulating beta receptors and/or G proteins, glucose transport blockers such as serutine or rutine, neuropeptide Y (NPY) antagonists capable of blocking NPY receptors at the adipocytes surface, cAMP and its cosmetically acceptable derivatives, adenylate cyclase enzyme active agents such as forskolin, agents modifying fat acids transport, lipolytic peptides and lipolytic proteins, like peptides or proteins such as the peptides derived from the parathyroidal hormone, described in particular in the patents FR 2788058 and FR 2781231.

Others examples of usable lipolytic agents include botanical and marine extracts: among plant extracts, there may more particularly be mentioned the extract of English ivy (*Hedera helix*), of Chinese thorowax (*Bupleurum chinensis*), of *Arnica* (*Arnica montana* L), of rosemary (*Rosmarinus officinalis* N), of marigold (*Calendula officinalis*), of sage (*Salvia officinalis* L), of ginseng (*Panax ginseng*), of Ginko biloba, of St.-John's-Wort (*Hyperycum perforatum*), of butcher's-broom (*Ruscus aculeatus* L), of European meadowsweet (*Filipendula ulmaria* L), of big-flowered Jarva tea (*Orthosiphon stamineus* Benth), of algae (*Fucus vesiculosus*), of birch (*Betula alba*), of green tea, of cola nuts (*Cola nitida*), of horse-chestnut, of bamboo, of spadeleaf (*Centella asiatica*), of heather, of fucus, of willow, of mouse-ear, extracts of escine, extracts of cangzhu, extracts of *Chrysanthellum indicum*, extracts of the plants of the *Armeniacea* genus, *Atractylodis platicodon, Sinnomenum, Pharbitidis, Flemingia*, extracts of *Coleus* such as *C. Forskohlii, C. blumei, C. esquirolii, C. scutellaroides, C. xanthantus* and *C.*

*Barbatus*, such as the extract of root of *Coleus barbatus*, extracts of *Ballote*, extracts of *Guioa*, of *Davallia*, of *Terminalia*, of *Barringtonia*, of *Trema*, of *antirobia, cecropia, argania, Dioscoreae* such as *Dioscorea opposita* or Mexican, as extracted of marine origin: extracts of algae or phytoplankton such as an extract of *Laminaria digitata*, diatoms, rhodysterol. All these extracts being able of course to be taken in mixtures.

The compositions according to the present disclosure can also contain in addition one or more additional active selected among: agents acting on the microcirculation (vasculoprotectors or vasodilators) such as the natural flavonoids, ruscogenines, esculosides, escine, nicotinates, heperidine methyl chalcone, butcher's-broom, essential oils of lavender or rosemary, the extracts of *Ammi visnaga*; antiglycation agents such as extracts of *Centella asiatica* and *Siegesbeckia*, silicium, amadorine, ergothioneine and its derivatives, hydroxystilbenes and their derivatives (e.g. resveratrol), vegetable extracts of the family of Ericaceae, in particular bilberry extracts (*Vaccinium angustifollium*), vitamin C and its derivatives, retinol and its derivatives.

Butylated Hydroxytoluene (BHT) and Butylated Hydroxyanisole (BHA)

The topical compositions of the present disclosure may comprise BHT or BHA.

In one embodiment, BHT and/or BHA is added from about 0.0001% to about 20% by weight of the composition, more preferably from about 0.001% to about 10%, even more preferably from about 0.01% to about 5%, and still more preferably from about 0.1% to about 0.5%.

Topical Anesthetics

The compositions of the present disclosure may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Desquamating/Keratolytic Actives

A desquamating/keratolytic active may be added to the compositions of the present disclosure. In one embodiment, the composition comprises from about 0.01% to about 10%, preferably from about 0.1% to about 5%, more preferably from about 0.5% to about 2%, by weight of the composition, of a desquamating/keratolytic active.

Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2hydroxynonanoic acid; 2-hydroxydecanoic acid; 2-hydroxyundecanoic acid; 2-hydroxydodecanoic acid (alpha-hydroxylauric acid); 2-hydroxytetradecanoic acid (alpha-hydroxymyristic acid); 2-hydroxyhexadecanoic acid (alpha-hydroxypalmitic acid); 2-hydroxyoctadecanoic acid (alpha-hydroxystearic acid); 2-hydroxyeicosanoic acid (alpha-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyl lactic acid); 2-phenyl 2-methyl 2-hydroxyethanoic acid (atrolactic acid); 2-(4'-hydroxyphenyl) 2-hydroxyethanoic acid; 2-(4'-chlorophenyl) 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3'-(2-hydroxyphenyl) 2-hydroxypropanoic acid; 3-(4'-hydroxyphenyl) 2-hydroxypropanoic acid; and 2-(3',4' dihydroxyphenyl), and 2-hydroxyethanoic acid, 5-n-octanoylsalicylic acid, 5-n-dodecanoyl salicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Preferred keratolytic agents are selected from the group comprising glycolic acid, tartaric acid, salicylic acid, citric acid, lactic acid, pyruvic acid, gluconic acid, glucuronic acid, malic acid, mandelic acid, oxalic acid, malonic acid, succinic acid, acetic acid, phenol, resorcine, retinoic acid, adapalene, trichloroacetic acid, 5-fluoro uracil, azelaic acid. Keratolytic agents are also the salts, esters, possible cis or trans forms, racemic mixtures and/or the relative dextrorotatory or levorotatory forms of the above listed compounds. Such substances can be used singularly or in associations with each other.

Other keratolytic agents suitable for use herein can include enzymatic exfoliant based on a protease called Keratoline™ and offered by Sederma.

One desquamation system that is suitable for use herein comprises salicylic acid and zwitterionic surfactants and is described in U.S. Pat. No. 5,652,228. Another desquamation system that is suitable for use herein contains sulfhydryl compounds and zwitterionic surfactants and is described in U.S. Pat. No. 5,681,852. Zwitterionic surfactants such as those described in this referenced patent can also be useful as desquamatory agents herein, with cetyl betaine being particularly preferred.

Anti-Acne Actives

The compositions of the present disclosure can comprise one or more anti-acne actives. Examples of useful anti-acne actives include resorcinol, sulfur, erythromycin, salicylic acid, benzoyl peroxide, dehydroacetic acid and zinc.

In one embodiment, when anti-acne compounds are present in the compositions of the instant present disclosure, the compositions comprise from about 0.0001% to about 50%, more preferably from about 0.001% to about 10%, still more preferably from about 0.01% to about 8%, and still more preferably from about 0.1% to about 5%, by weight of the composition, of the anti-acne compound.

Anti-Wrinkle Actives/Anti-Atrophy Actives

The compositions of the present disclosure can comprise a one or more anti-wrinkle actives or anti-atrophy actives. Exemplary anti-wrinkle/anti-atrophy actives suitable for use in the compositions of the present disclosure include sulfur-containing D and L amino acids and their derivatives and salts, particularly the N-acetyl derivatives, a preferred example of which is N-acetyl-L-cysteine; thiols, e.g. ethane thiol, hydroxy acids (e.g., alpha-hydroxy acids such as lactic acid and glycolic acid or beta-hydroxy acids such as salicylic acid and salicylic acid derivatives such as the octanoyl derivative, lactobionic acid), keto acids (e.g., pyruvic acid), phytic acid, ascorbic acid (vitamin C), stilbenes, cinnamates, resveratrol, kinetin, zeatin, dimethylaminoethanol, peptides from natural sources (e.g., soy peptides), and salts of sugar acids (e.g., Mn gluconate, Zn gluconate), lipoic acid; lysophosphatidic acid, skin peel agents (e.g., phenol and the like), vitamin B3 compounds and retinoids and other vitamin B compounds (e.g., thiamine (vitamin B1), pantothenic acid (vitamin B5), riboflavin (vitamin B2), and their derivatives and salts (e.g., HCL salts or calcium salts).

In one embodiment, when anti-wrinkle/anti-atrophy compounds are present in the compositions of the instant present disclosure, the compositions comprise from about 0.0001% to about 50%, more preferably from about 0.001% to about 10%, still more preferably from about 0.01% to about 8%, and still more preferably from about 0.1% to about 5%, by weight of the composition, of the anti-wrinkle/anti-atrophy compound.

Anti-Oxidants/Racial Scavengers

The compositions of the present disclosure can include an anti-oxidant/radical scavenger. In one embodiment, the composition comprises from about 0.01% to about 10%, more preferably from about 0.1% to about 5%, of an anti-oxidant/radical scavenger.

Anti-oxidants/radical scavengers such as retinyl palmitate, ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, amines (e.g., N,N-diethylhydroxylamine, amino-guanidine), nordihydroguaiaretic acid, bioflavonoids, sulfhydryl compounds (e.g., glutathione), dihydroxy fumaric acid and its salts, lysine pidolate, arginine pilolate, amino acids, silymarin, lysine, 1-methionine, proline, superoxide dismutase, sorbic acids and its salts, lipoic acid, olive extracts, tea extracts, polyphenols such as proanthocyanidine from pine bark, carotenoids, curcumin compounds such as tetrahydrocurcumin, OCTA (L-2-oxo-4-thiazolidine carboxylic acid), glutathione, melanin, rosemary extracts and grape skin/seed extracts may be used.

Humectants, Moisturizers and Conditioning Agents

The compositions of the present disclosure can contain a safe and effective amount of a conditioning agent selected from, for example, humectants, moisturizers, and skin conditioners. A variety of these materials can be employed and in one embodiment can be present at a level of from about 0.01% to about 20%, more preferably from about 0.1% to about 10%, and still more preferably from about 0.5% to about 7%, by weight of the composition. These materials can include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyhydroxy alcohols such as sorbitol, mannitol, xylitol, erythritol, glycerol, hexanetriol, butanetriol, propylene glycol, butylene glycol, hexylene glycol and the like, polyethylene glycols, sugars (e.g., melibiose), starches, sugar and starch derivatives (e.g., alkoxylated glucose, fructose, glucosamine), hyaluronic acid, lactamide monoethanolamine, acetamide monoethanolamine, panthenol, allantoin, petroleum and mixtures thereof. Also useful herein are the propoxylated glycerols described in U.S. Pat. No. 4,976,953.

Also useful are various C1-C30 monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin, glycerol, and combinations thereof.

Humectants can be selected from the group consisting of polyhydric alcohols, water soluble alkoxylated nonionic polymers, and mixtures thereof. Polyhydric alcohols useful herein include polyhydroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, PPG-12/SMDI copolymer and mixtures thereof.

Active Oxygen Generation Inhibitors

The compositions of the present disclosure may also comprise an active oxygen generation inhibitor selected from the group comprising quercetin, rutin, taxifolin, kaempferol, myricetin, curcumin, resveratrol, arecoline, apigenin, wogonin, luteolin, tectorigenin, and a mixture thereof.

This active oxygen generation inhibitor may be contained in an amount of about 0.001% to about 5%, more preferably in an amount of about 0.01% to about 3% %, by weight of the composition.

Chelators

The compositions of the present disclosure may also comprise a chelator or chelating agent. As used herein, "chelator" or "chelating agent" means an active agent capable of removing a metal ion from a system by forming a complex so that the metal ion cannot readily participate in or catalyze oxygen radical formation. In one embodiment, a chelating agent is added to a composition of the present disclosure, preferably from about 0.00001% to about 10%, more preferably from about 0.001% to about 5%, by weight of the composition. Examples of chelating agents include N-hydroxysuccinimide, EDTA, Disodium EDTA, NTA, deferoxamine, hydroxamic acids and their salts, phytic acid, phytate, gluconic acid and its salts, transferrine, lactoferrin; furildioxime and derivatives thereof.

Anti-Inflammatory Agents

An anti-inflammatory agent may be added to the compositions of the present disclosure. In one embodiment, an anti-inflammatory agent is added at a level of from about 0.01% to about 10%, preferably from about 0.5% to about 5%, by weight of the composition. The exact amount of anti-inflammatory agent to be used in the compositions will depend on the particular anti-inflammatory agent utilized since such agents vary widely in potency Steroidal anti-inflammatory agents can include, but are not limited to, corticosteroids such as hydrocortisone. In addition, non-steroidal anti-inflammatory agents can be useful herein. The varieties of compounds encompassed by this group are well known to those skilled in the art. Specific non-steroidal anti-inflammatory agents that can be useful in the composition of the present disclosure include, but are not limited to, oxicams such as piroxicam, salicylates such as aspirin; acetic acid derivatives, such as felbinac, fenamates, such as etofenamate, flufenamic, mefenamic, meclofenamic, acids;

propionic acid derivatives, such as ibuprofen, naproxen, pyrazoles, and mixtures thereof. Mixtures of these non-steroidal anti-inflammatory agents may also be employed, as well as the dermatologically acceptable salts and esters of these agents.

Finally, so-called "natural" anti-inflammatory agents are useful in methods of the present disclosure. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum* extract (Kava Kava from *Bacopa monieri* extract (Bacocalmine™) and sea whip extract, may be used. Anti-inflammatory agents useful herein include allantoin and compounds of the Licorice (the plant genus/species *Glycyrrhiza glabra* family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred. Additional anti inflammatory agents include diosgenol, saponines, sapogenines, lignanes, triterpenes saponosides and genines.

Tanning Actives

The compositions of the present disclosure can comprise a tanning active. In one embodiment, the composition comprises from about 0.1% to about 20%, more preferably from about 2% to about 7%, and even more preferably from about 3% to about 6%, by weight of the composition, of a tanning active. A preferred tanning active is dihydroxyacetone, which is also known as DHA or 1,3-dihydroxy-2-propanone.

Skin Lightening Agents

The compositions of the present disclosure may contain a skin lightening agent. When used, the compositions preferably contain from about 0.001% to about 10%, more preferably from about 0.02% to about 5%, also preferably from about 0.05% to about 2%, by weight of the composition, of a skin lightening agent. Suitable skin lightening agents include those known in the art, including kojic acid, hydroquinone, aminophenol derivatives, N-cholesteryloxycarbonyl-para-aminophenol and N-ethyloxycarbonyl-para-aminophenol; iminophenol derivatives, L-2-oxothiazolidine-4-carboxylic acid or procysteine, and also its salts and esters, arbutin, tranexamic acid, ascorbic acid and derivatives thereof (e.g., magnesium ascorbyl phosphate or sodium ascorbyl phosphate, ascorbyl glucoside and the like (such as AA2G from Hayashibara)), and extracts (e.g., mulberry extract, placental extract, skullcap extract *brousonetia* extract, oil soluble liquorice extract (such as these available from Maruzen), oil soluble liquorice extract (*glycyrrhiza*, chamomile extract (such as these available from Kao)), m-Tranexamic acid/vitamin C ethyl (such as these available from Shiseido), adenosine monophosphate disodium (APM offered by Otsuka), ellagic acid (Lion), rucinol (Pola), ethyl ascorbyl ether).

Antimicrobial, Antibacterial and Antifungal Actives

The compositions of the present disclosure can comprise one or more anti-fungal or anti-microbial actives. A safe and effective amount of an antimicrobial or antifungal active can be added to the present compositions. In one embodiment, the composition comprises from about 0.001% to about 10%, preferably from about 0.01% to about 5%, and more preferably from about 0.05% to about 2%, by weight of the composition, of an antimicrobial or antifungal active.

Suitable anti-microbial actives include coal tar, sulfur, whitfield's ointment, castellani's paint, aluminum chloride, gentian violet, octopirox (piroctone olamine), 3,4,4'-trichlorocarbanilide (trichlosan), triclocarban, ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazolinbne and azoles, and combinations thereof. Preferred anti-microbials include itraconazole, ketoconazole, selenium sulphide and coal tar. In one embodiment, one or more anti-fungal or anti-microbial active is combined with an anti-dandruff active selected from polyvalent metal salts of pyrithione.

a. Azoles

Azole anti-microbials include imidazoles such as benzimidazole, benzothiazole, bifonazole, butoconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein are ketoconazole and climbazole.

b. Selenium Sulfide

Selenium sulfide is a particulate anti-dandruff agent suitable for use in the anti-microbial compositions of the present disclosure, effective concentrations of which range from about 0.1% to about 4%, by weight of the composition, preferably from about 0.3% to about 2.5%, more preferably from about 0.5% to about 1.5.

c. Sulfur

Sulfur may also be used as a particulate anti-microbial/anti-dandruff agent in the anti-microbial compositions of the present disclosure. Effective concentrations of the particulate sulfur are typically from about 1% to about 4%, by weight of the composition, preferably from about 2% to about 4%.

d. Additional Anti Microbial Actives

Additional anti-microbial actives of the present disclosure may include one or more keratolytic agents such as salicylic acid, extracts of *melaleuca* (tea tree) and charcoal. The present disclosure may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Preferred examples of actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, miconazole, ketoconazole, neomycin sulfate, and mixtures thereof.

Thickening Agents (Including Thickeners and Gelling Agents)

The compositions of the present disclosure can comprise one or more thickening agents. In one embodiment, a thickening agent is present at a level of from about 0.05% to about 10%, preferably from about 0.1% to about 5%, and more preferably from about 0.25% to about 4%, by weight of the composition. Nonlimiting classes of thickening agents include those selected from the following:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228, 868.

c. Polyacrylamide Polymers

The compositions of the present disclosure can optionally contain polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties and may be used in concentration ranges between 1 and 99%, most advantageously between 5 and 15%.

d. Polysaccharides

A wide variety of polysaccharides can be useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™ CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Antiperspirant Actives

Antiperspirant actives may also be included in the compositions of the present disclosure. Suitable antiperspirant actives include astringent metallic salts, especially the inorganic and organic salts of aluminum zirconium and zinc, as well as mixtures thereof. Particularly preferred are the aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, when antiperspirant actives are present in the compositions of the instant present disclosure, the compositions comprise from about 0.01% to about 50%, more preferably from about 0.1% to about 40%, and still more preferably from about 1% to about 30%, by weight of the composition, of the antiperspirant compound.

Detersive Surfactants

The compositions of the present disclosure can include detersive surfactant from about 1% to about 90%, more preferably from about 5% to about 10%. The detersive surfactant component can be included to provide cleaning performance to the composition. The detersive surfactant component in turn can comprise anionic detersive surfactant, zwitterionic or amphoteric detersive surfactant, or a combination thereof. Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, and generally can range from about 5% to about 50%, preferably from about 8% to about 30%, more preferably from about 10% to about 25%, even more preferably from about 12% to about 22%.

Preferred anionic surfactants suitable for use in the compositions are the alkyl and alkyl ether sulfates. Other suitable anionic detersive surfactants are the water-soluble salts of organic, sulfuric acid reaction products, alkoyl isethionates, sodium or potassium salts of fatty acid amides of methyl tauride, olefin sulfonates, and beta-alkyloxy alkane sulfonates. Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably ranges from about 0.5% to about 20%, preferably from about 1% to about 10%. Non limiting examples of suitable zwitterionic or amphoteric surfactants are described in U.S. Pat. Nos. 5,104,646 and 5,106,609.

Amphoteric detersive surfactants include derivatives of aliphatic secondary and tertiary amines.

The compositions of the present disclosure may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M.C. Publishing Co., and U.S. Pat. Nos. 3,929,678, 2,658,072; 2,438,091; 2,528,378.

Cationic, Anionic and Amphoteric Polymers

The compositions of the present disclosure can comprise polymers which may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or non-ionic.

When included, concentrations of the cationic polymer in the composition can typically range from about 0.05% to about 3%, preferably from about 0.075% to about 2.0%, more preferably from about 0.1% to about 1.0 a. Cationic Polymers

Suitable cationic polymers for use in the compositions of the present disclosure contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of such polymers are described in the CTFA.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide; amine derivatives of methacrylic acid or amine derivatives of methacrylamide derived from methacrylic acid or methacrylamide and a dialkylalkanolamine having C1-C6 alkyl groups such as dimethylaminoethyl (meth)acrylate, diethylaminoethyl (meth)acrylate, dimethylaminopropyl (meth)acrylate, or dimethylaminopropyl (meth)acrylamide.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47). Preferred cationic substituted monomers are the cationic substituted dialkylaminoalkyl acrylamides, dialkylaminoalkyl methacrylamides, and combinations thereof. A non limiting example is polymethyacrylamidopropyl trimonium chloride, available under the tradename Polycare 133, from Rhone-Poulenc.

Other suitable cationic polymers for use in the composition include polysaccharide polymers, such as cationic cellulose derivatives and cationic starch derivatives.

Preferred cationic cellulose polymers are salts of hydroxyethyl cellulose reacted with trimethyl ammonium substituted epoxide, referred to in the industry (CTFA) as Polyquaternium 10 and available from Amerchol Corp. in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

b. Anionic Polymers

Examples of anionic polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

c. Amphoteric Monomers

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth)acrylamide, as discussed above, modified with propanesultone.

Nonionic Polymers

The compositions herein can comprise nonionic polymers. For instance, polyalkylene glycols having a molecular weight of more than about 1000 can be used. Preferred polyethylene glycol polymers can include PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Examples of nonionic monomers are acrylic or methacrylic acid esters of C1-C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl (meth)acrylate, methoxy ethyl (meth)acrylate, butoxyethyl (meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof.

Hair Conditioning Agents

Conditioning agents include any material which is used to give a particular conditioning benefit to keratinous tissue. For instance, in hair treatment compositions, suitable conditioning agents include those which deliver one or more benefits relating to shine, softness, combability, antistatic properties, wet-handling, damage, manageability, body, and greasiness. Conditioning agents useful in the compositions of the present disclosure can comprise a water insoluble, water dispersible, non-volatile liquid that forms emulsified, liquid particles. Suitable conditioning agents for use in the composition include those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

When included, the concentration of the conditioning agent in the composition can be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

a. Silicones

The conditioning agent of the compositions of the present disclosure is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609.

Background material on silicones including sections discussing silicone fluids, gums, and resins, as well as manufacture of silicones, are found in Encyclopedia of Polymer Science and Engineering, vol. 15, 2d ed., pp 204-308, John Wiley & Sons, Inc. (1989).

b. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present disclosure include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

c. Amino and Cationic Silicones

Cationic silicone fluids suitable for use in the compositions of the present disclosure include, but are not limited to, the polymer known as "trimethylsilylamodimethicone". Other silicone cationic polymers which may be used in the compositions of the present disclosure may be UCARE SILICONE ALE56™, available from Union Carbide.

d. Silicone Gums

Other silicone fluids suitable for use in the compositions of the present disclosure are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76. Specific non-limiting examples of silicone gums for use in the compositions of the present disclosure include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

e. High Refractive Index Silicones

Other non-volatile, insoluble silicone fluid conditioning agents that are suitable for use in the compositions of the present disclosure are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

When high refractive index silicones are used in the compositions of the present disclosure, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the compositions of the present disclosure are disclosed in U.S. Pat. Nos. 2,826,551, 3,964,500, 4,364,837, British Pat. No. 849,433, and Silicon Compounds, Petrarch Systems, Inc. (1984).

f. Silicone Resins

Silicone resins may be included in the silicone conditioning agent of the compositions of the present disclosure. These resins are highly cross-linked polymeric siloxane systems. The cross-linking is introduced through the incorporation of trifunctional and tetrafunctional silanes with monofunctional or difunctional, or both, silanes during manufacture of the silicone resin.

Organic Conditioning Oils

Compositions of the present disclosure may also comprise organic conditioning oil. In one embodiment, from about 0.05% to about 20%, preferably from about 0.08% to about 1.5%, more preferably from about 0.1% to about 1%, of at least one organic conditioning oil is included as a conditioning agent, either alone or in combination with other conditioning agents, such as the silicones (described herein).

a. Hydrocarbon Oils

Suitable organic conditioning oils for use as conditioning agents in the compositions of the present disclosure include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C12 to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation, hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. Another example is hydrogenated polyisobute or liquid isoparaffine.

b. Polyolefins

Organic conditioning oils for use in the compositions of the present disclosure can also include liquid polyolefins, more preferably liquid poly-α-olefins, more preferably hydrogenated liquid poly-α-olefins. Polyolefins for use herein are prepared by polymerization of C4 to about C14 olefenic monomers, preferably from about C6 to about C12.

Preferred non-limiting examples of olefenic monomers for use in preparing the polyolefin liquids herein include ethylene, propylene, 1-butene, 1-pentene, 1-hexene to 1-hexadecenes, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents.

c. Fatty Esters

Other suitable organic conditioning oils for use as the conditioning agent in the compositions of the present disclosure include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present disclosure are mono-carboxylic acid esters of the general formula R' COOR, wherein R' and R are alkyl or alkenyl radicals, and the sum of carbon atoms in R' and R is at least 10, preferably at least 22.

Still other fatty esters suitable for use in the compositions of the present disclosure are di- and tri-alkyl and alkenyl esters of carboxylic acids, such as esters of C4 to C8 dicarboxylic acids (e.g. C1 to C22 esters, preferably C1 to C6, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present disclosure are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present disclosure are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as C10 to C22 carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present disclosure are water insoluble synthetic fatty esters.

Specific non-limiting examples of suitable synthetic fatty esters for use in the compositions of the present disclosure include: P-43 (C8-C10 triester of trimethylolpropane), MCP-684 (tetraester of 3,3 diethanol-1,5 pentadiol), MCP 121 (C8-C10 diester of adipic acid), all of which are available from Mobil Chemical Company.

Anti-Dandruff Actives

The compositions of the present disclosure may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts, especially 1-hydroxy-2-pyridinethione salts. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT").

Humectant

The compositions of the present disclosure may contain a humectant. Humectants can be selected from the group consisting of polyhydric alcohols, water soluble alkoxylated nonionic polymers, and mixtures thereof. Humectants, when used herein, are preferably used at levels of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as PEG-200, PEG-400, PEG-600, PEG-1000 (CTFA names), and mixtures thereof.

Suspending Agent

The compositions of the present disclosure may further comprise a suspending agent, preferably at concentrations effective for suspending water-insoluble material in dispersed form in the compositions or for modifying the viscosity of the composition. Such concentrations can preferably range from about 0.1% to about 10%, more preferably from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, nitro cellulose, sodium carboxymethyl cellulose, crystalline cellulose, cellulose powder, polyvinylpyrrolidone, polyvinyl alcohol, guar gum, hydroxypropyl guar gum, arabia gum, galactan, carob gum, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid. Actives aforementioned as thickening agents can also be used herein as suspending agents.

Commercially available viscosity modifiers highly useful herein include Carbomers with tradenames Carbopol 934, Carbopol 940, Carbopol 950, Carbopol 980, and Carbopol 981, all available from B.F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, long chain acyl derivatives and mixtures thereof. These suspending agents are described in U.S. Pat. No. 4,741,855. These preferred suspending agents include ethylene glycol esters of fatty acids, alkanol amides of fatty acids, long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® available from Rheox, Inc.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Terpene Alcohol

The compositions of the present disclosure may comprise a terpene alcohol or combinations of terpene alcohols. As used herein, "terpene alcohol" refers to organic compounds composed of two or more 5-carbon isoprene units [CH2=C(CH3)-CH=CH2] with a terminal hydroxyl group. Preferably, the composition can comprise from about 0.001% to about 50%, preferably from about 0.01% to about 20%, more preferably from about 0.1% to about 15%, even more preferably from about 0.1% to about 10%, still more preferably from about 0.5% to about 5%, and still more preferably from about 1% to about 5%, by weight of the composition, of the terpene alcohol.

Examples of terpene alcohols that can be useful herein include farnesol, derivatives of farnesol, isomers of farnesol, geraniol, derivatives of geraniol, isomers of geraniol, phytantriol, derivatives of phytantriol, isomers of phytantriol, and mixtures thereof. A preferred terpene alcohol for use herein is farnesol.

a. Farnesol and Derivatives Thereof.

Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco) and trans-trans-farnesol (Sigma Chemical Company). A suitable derivative of farnesol is farnesyl acetate which is commercially available from Aldrich Chemical Company.

b. Geraniol and Derivatives Thereof.

Geraniol is the common name for the chemical known as 3,7-dimethyl-2,6-octadien-1-ol. As used herein, "geraniol" includes isomers and tautomers of such. Geraniol is commercially available from Aldrich Chemical Company. Suitable derivatives of geraniol include geranyl acetate, geranylgeraniol, geranyl pyrophosphate, and geranylgeranyl pyrophosphate, all of which are commercially available from Sigma Chemical Company. For example, geraniol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

c. Phytantriol and Derivatives Thereof.

Phytantriol is the common name for the chemical known as 3,7,11,15 tetramethylhexadecane-1,2,3,-triol. Phytantriol is commercially available from BASF. For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

Enzymes, Enzyme Inhibitors and Enzyme Activators (Coenzymes)

The compositions of the present disclosure may contain a safe and effective amount of one or more enzymes, enzyme inhibitors or enzyme activators (coenzymes). Examples of enzymes are lipases, proteases, catalase, superoxide-dismutase, amylases, glucuronidases, peroxidases, in particular glutathione peroxidase or lactoperoxidase, ceramidases, hyaluronidases. All of these enzymes may be obtained by extraction or by fermentation biotechnology processes.

Examples of enzyme inhibitors include trypsine inhibitors, Bowmann Birk inhibitor, chymotrypsin inhibitors, botanical extracts with or without tannins, flavonoids, quercetin which inhibit enzymatic activity. Enzyme preparations can be found, for instance, in the product named VENUCEANE proposed by SEDERMA, France (WO 02/066668). Enzyme activators and coenzymes include Coenzyme A, coenzyme Q10 (ubiquinone), glycyrrhizidine, berberine, chrysine.

Carrier

The compositions of the present disclosure can comprise an orally or a dermatologically acceptable carrier, or injectable liquid, depending upon the desired product form.

Dermatologically Acceptable Carrier

The topical compositions of the present disclosure can also comprise a dermatologically acceptable carrier for the composition. In one embodiment, the carrier is present at a level of from about 50% to about 99.99%, preferably from about 60% to about 99.9%, more preferably from about 70% to about 98%, and even more preferably from about 80% to about 95%, by weight of the composition.

The carrier can be in a wide variety of forms. Non-limiting examples include simple solutions (water or oil based), emulsions, and solid forms (gels, sticks). For example, emulsion carriers can include, but are not limited to, oil-in-water, water-in-oil, water-in-silicone, water-in-oil-in-water, and oil-in-water-in-silicone emulsions.

Depending upon the desired product form, preferred carriers can comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition. In one embodiment, oil-in-water emulsions are especially preferred.

Emulsions according to the present disclosure can contain an aqueous phase and a lipid or oil. Lipids and oils may be derived from animals, plants, or petroleum and may be natural or synthetic (i.e., man-made). Preferred emulsions can also contain a humectant, such as glycerin. Emulsions can further comprise from about 0.1% to about 10%, more preferably from about 0.2% to about 5%, of an emulsifier, based on the weight of the composition. Emulsifiers may be nonionic, anionic or cationic. Suitable emulsifiers are disclosed in, for example, U.S. Pat. Nos. 3,755,560, 4,421,769, and McCutcheon's Detergents and Emulsifiers, North American Edition, pages 317-324 (1986). Suitable emulsions may have a wide range of viscosities, depending on the desired product form.

The compositions of the present disclosure can be in the form of pourable liquids (under ambient conditions). The compositions can therefore comprise an aqueous carrier, which is typically present at a level of from about 20% to about 95%, preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The emulsion may also contain an anti-foaming agent to minimize foaming upon application to the keratinous tissue. Anti-foaming agents include high molecular weight silicones and other materials well known in the art for such use.

Preferred water-in-silicone and oil-in-water emulsions are described in greater detail below.

Water-in-Silicone Emulsion

Water-in-silicone emulsions can contain a continuous silicone phase and a dispersed aqueous phase.

a. Continuous Silicone Phase

Preferred water-in-silicone emulsions of the present disclosure can contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the active ingredients of the present disclosure. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid, Dow Corning® 225 fluid, and Dow Corning® 200 fluids Examples of suitable alkyl-substituted dimethicones include cetyl dimethicone and lauryl dimethicone.

Cyclic polyalkylsiloxanes suitable for use in the composition include commercially available cyclomethicones such as Dow Corning® 244 fluid, Dow Corning® 344 fluid, Dow Corning® 245 fluid and Dow Corning® 345 fluid.

Also useful are materials such as trimethylsiloxysilicate. A commercially available trimethylsiloxysilicate is sold as a mixture with dimethicone as Dow Corning® 593 fluid. Dimethiconols are also suitable for use in the composition. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

b. Dispersed Aqueous Phase

The topical compositions of the present disclosure can contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelating ingredients, gums, water-soluble or dispersible alcohols and polyols, buffers, preservatives, sunscreening agents, colorings, and the like.

The topical compositions of the present disclosure will typically contain from about 25% to about 90%, preferably from about 40% to about 80%, more preferably from about 60% to about 80%, water in the dispersed aqueous phase by weight of the composition.

c. Emulsifier for Dispersing the Aqueous Phase

The water-in-silicone emulsions of the present disclosure may preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present disclosure, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Dimethicone copolyol emulsifiers useful herein are described, for example, in U.S. Pat. No. 4,960,764, EP 330,369. Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. Nos. 5,011,681; 4,421,769; and 3,755,560.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

d. Silicone Elastomer

The compositions of the present disclosure may also include from about 0.1% to about 30%, by weight of the composition, of a silicone elastomer component. Preferably, the composition includes from about 1% to about 30%, more preferably from about 2% to about 20%, by weight of the composition, of the silicone elastomer component.

Suitable for use herein are silicone elastomers, which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Addition reaction-curing organopolysiloxane compositions are preferred for their rapid curing rates and excellent uniformity of curing. A particularly preferred addition reaction-curing organopolysiloxane composition is prepared from: a) an organopolysiloxane having at least 2 lower alkenyl groups in each molecule; b) an organopolysiloxane having at least 2 silicon-bonded hydrogen atoms in each molecule; and c) a platinum-type catalyst.

The compositions of the present disclosure may include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomers can notably be chosen from the crosslinked polymers described in U.S. Pat. Nos. 5,412,004, 5,837,793, and 5,811,487. In addition, an emulsifying elastomer comprised of dimethicone copolyol crosspolymer (and) dimethicone is available from Shin Etsu under the tradename KSG-21.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present disclosure and processes for making them are further described in U.S. Pat. Nos. 4,970,252, 5,760,116, and 5,654,362.

Commercially available elastomers preferred for use herein are Dow Corning's 9040 silicone elastomer blend, Shin Etsu's KSG-21, and mixtures thereof.

e. Carrier for Silicone Elastomer

The topical compositions of the present disclosure may include from about 1% to about 80%, by weight of the composition, of a suitable carrier for the for the crosslinked organopolysiloxane elastomer component described above. The carrier, when combined with the cross-linked organopolysiloxane elastomer particles of the present disclosure, serves to suspend and swell the elastomer particles to provide an elastic, gel-like network or matrix. The carrier for the cross-linked siloxane elastomer is liquid under ambient conditions, and preferably has a low viscosity to provide for improved spreading on the skin.

Concentrations of the carrier in the cosmetic compositions of the present disclosure will vary primarily with the type and amount of carrier and the cross-linked siloxane elastomer employed. Preferred concentrations of the carrier are from about 5% to about 50%, more preferably from about 5% to about 40%, by weight of the composition.

The carrier for the cross-linked siloxane elastomer includes one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 (cal/cm3>) 05.

f. Non-Polar, Volatile Oils

The composition of the present disclosure may include non-polar, volatile oils. The non-polar, volatile oil tends to impart highly desirable aesthetic properties to the compositions of the present disclosure. Consequently, the non-polar, volatile oils are preferably utilized at a fairly high level. Non-polar, volatile oils particularly useful in the present disclosure are silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. Examples of preferred non-polar, volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals). Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

g. Relatively Polar, Non-Volatile Oils

The composition of the present disclosure may include relatively polar, non-volatile oils. The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils potentially useful in the present disclosure are disclosed, for example, in Cosmetics, Science, and Technology, Vol. 1, 27-104 edited by Balsam and Sagarin, 1972; U.S. Pat. Nos. 4,202,879 and 4,816,261. Relatively polar, non-volatile oils useful in the present disclosure are preferably selected from silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

h. Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present disclosure are essentially non-volatile polysiloxanes, paraffinic hydrocarbon oils, and mixtures thereof.

Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-oil emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-oil emulsion. The preferred oil-in-water emulsions comprises from about 25% to about 98%, preferably from about 65% to about 95%, more preferably from about 70% to about 90% water by weight of the total composition.

In addition to a continuous water phase and dispersed oil or silicone phase, these oil-in-water compositions also comprise an emulsifier to stabilize the emulsion. Emulsifiers useful herein are well known in the art, and include non-ionic, anionic, cationic, and amphoteric emulsifiers. Non-limiting examples of emulsifiers useful in the oil-in-water emulsions of this present disclosure are given in McCutcheon's, Detergents and Emulsifiers, North American Edition (1986), U.S. Pat. Nos. 5,011,681; 4,421,769; and 3,755,560. Examples of suitable oil-in-water emulsion carriers are described in U.S. Pat. Nos. 5,073,371, and 5,073,372. An especially preferred oil-in-water emulsion, containing a structuring agent, hydrophilic surfactant and water, is described in detail hereinafter.

a. Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this present disclosure contain from about 0.5% to about 20%, more preferably from about 1% to about 10%, even more preferably from about 1% to about 5%, by weight of the composition, of a structuring agent.

The preferred structuring agents of the present disclosure include stearic acid, palmitic acid, stearyl alcohol, cetyl alcohol, behenyl alcohol, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present disclosure are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

b. Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from nonionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula (S)n-O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel). Other useful nonionic surfactants include the condensation products of alkylene oxides with fatty acids (i.e. alkylene oxide esters of fatty acids), the condensation products of alkylene oxides with 2 moles of fatty acids (i.e. alkylene oxide diesters of fatty acids), the condensation products of alkylene oxides with fatty alcohols (i.e. alkylene oxide ethers of fatty alcohols), the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants. An especially preferred surfactant corresponding to the above structure is coconut alkyl N-methyl glucoside amide. Processes for making compositions containing polyhydroxy fatty acid amides are disclosed, for example in U.S. Pat. Nos. 2,965,576; 2,703,798, and 1,985,424.

Preferred among the nonionic surfactants are those selected from the group consisting of steareth-21, ceteareth-20, ceteareth-12, sucrose cocoate, steareth-100, PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the tradename Arlatone 2121.

Other suitable surfactants useful herein include a wide variety of cationic, anionic, zwitterionic, and amphoteric surfactants such as are known in the art and discussed more fully below. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds, examples of which are described in U.S. Pat. Nos. 5,151,209; 5,151,210; 5,120,532; 4,387,090; 3,155,591; 3,929,678; 3,959,461; McCutcheon's, Detergents & Emulsifiers, (North American edition 1979) M.C. Publishing Co.; and Schwartz, et al., Surface Active Agents, Their Chemistry and Technology, New York: Interscience Publishers, 1949. Nonlimiting examples of these cationic emulsifiers include cetearyl olivate, sorbitan olivate, stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintain to enhance physical and chemical stability, especially when such a combination contains ionic and/or highly polar solvents.

A wide variety of anionic surfactants can also be useful herein. Nonlimiting examples of anionic surfactants include the alkoyl isethionates, and the alkyl and alkyl ether sulfates. The reaction products of fatty acids esterified with isethianonic acid and neutralized, i.e. the alkoyl isethionates typically have the formula RCO—OCH2CH2SO3M wherein R is alkyl or alkenyl of from about 10 to about 30 carbon atoms, and M is a water-soluble cation such as ammonium, sodium, potassium and triethanolamine. For example, the fatty acids are derived from coconut or palm kernel oil. Nonlimiting examples of these isethionates include the alkoyl isethionates selected from ammonium cocoyl isethionate, sodium cocoyl isethionate, sodium lauroyl isethionate, sodium stearoyl isethionate, and mixtures thereof. Also suitable are salts of fatty acids, amids of methyl taurides. Other similar anionic surfactants are described in U.S. Pat. Nos. 2,486,921; 2,486,922 and 2,396,278.

Another suitable class of anionic surfactants are the water-soluble salts of the organic, sulfuric acid reaction products of the general formula: R1-SO3-M wherein R1 is chosen from the group including a straight or branched chain, saturated aliphatic hydrocarbon radical having from about 8 to about 24, preferably about 10 to about 16, carbon atoms; and M is a cation described hereinbefore. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate. Other anionic surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions are the beta-alkyloxy alkane sulfonates. These surfactants conform to the formula where R1 is a straight chain alkyl group having from about 6 to about 20 carbon atoms, R2 is a lower alkyl group having from about 1 to about 3 carbon atoms, preferably 1 carbon atom, and M is a water-soluble cation as described hereinbefore. Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853. Amphoteric and zwitterionic surfactants are also useful herein. Examples of amphoteric and zwitterionic surfactants which can be used in the compositions of the present disclosure are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH2)mCO2M]2 and RNH (CH2)mCO2M wherein m is from 1 to 4, R is a C8-C22 alkyl or alkenyl, and M is H, alkali metal, alkaline earth metal ammonium, or alkanolammonium. Preferred amphoteric surfactants for use in the present disclosure include cocoamphoacetate, cocoamphodiacetate, lauroamphoacetate, lauroamphodiacetate, and mixtures thereof. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072; N-higher alkyl aspartic acids such as those produced according to the teaching of U.S. Pat. No. 2,438,091; and the products sold under the tradename "Miranol" and described in U.S. Pat. No. 2,528,378. Other examples of useful amphoterics include phosphates, such as coamidopropyl PG-dimonium chloride phosphate (commercially available as Monaquat PTC, from Mona Corp.).

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alphacarboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

c. Water Emollient

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject present disclosure, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) contains numerous examples of materials suitable as an emollient. A preferred emollient is glycerin. Glycerin is preferably used in an amount of from about 0.001 to about 30%, more preferably from about 0.01 to about 20%, still more preferably from about 0.1 to about 10%, e.g., 5%.

Lotions and creams according to the present disclosure generally contain a solution carrier system and one or more emollients. Lotions and creams typically contain from about 1% to about 50%, preferably from about 1% to about 20%, of emollient; from about 50% to about 90%, preferably from about 60% to about 80%, water; the polypeptides, according to the present disclosure, and the additional skin care active (or actives) in the above described amounts. Creams are generally thicker than lotions due to higher levels of emollients or higher levels of thickeners.

Ointments of the present disclosure may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, Cosmetics, Science and Technology, 2nd Edition, Vol. 1, pp. 72-73 (1972), and/or an emollient. For example, an ointment may contain from about 2% to about 10% of an emollient; from about 0.1% to about 2% of a thickening agent; and the polypeptide and the additional skin care active (or actives) in the above described amounts.

Compositions of this present disclosure useful for cleansing ("cleansers") can be formulated with a suitable carrier, e.g., as described above, and preferably comprise from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. See U.S. Pat. No. 4,800,197 for exemplary surfactants useful herein. Examples of a broad variety of additional surfactants useful herein are described in McCutcheon's Detergents and Emulsifiers, North American Edition (1986), published by Allured Publishing Corporation. The cleansing compositions can optionally contain, at their art-established levels, other materials which are conventionally used in cleansing compositions.

As used herein, the term "foundation" refers to a liquid, semi-liquid, semi-solid, or solid skin cosmetic which includes, but is not limited to lotions, creams, gels, pastes, cakes, and the like. Typically, the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present disclosure include a dermatologically acceptable carrier and may include conventional ingredients such as oils, colorants, pigments, emollients, fragrances, waxes, stabilizers, and the like. Exemplary carriers and such other ingredients which are suitable for use herein are described, for example, in WO96/33689, and GB 2274585.

Orally Acceptable Carrier

The compositions of the present disclosure can also comprise an orally acceptable carrier if they are to be ingested. Any suitable orally ingestible carrier or carrier form, as known in the art or otherwise, can be used. Non-limiting examples of oral personal care compositions can include, but are not limited to, tablets, pills, capsules, drinks, beverages, syrups, granules, powders, vitamins, supplements, health bars, candies, chews, and drops.

Injectible Liquid

The compositions of the present disclosure can also comprise a liquid that is acceptable for injection in and/or under the skin if the composition is to be injected. Any suitable acceptable liquid as known in the art or otherwise can be used.

Composition Preparations

The compositions useful for the methods of the present disclosure are generally prepared by conventional methods such as are known in the art of making topical and oral compositions and compositions for injection. Such methods typically can involve mixing of the ingredients in one or more steps to a relatively uniform state, with or without heating, cooling, application of vacuum, and the like.

The physical form of the compositions according to the present disclosure is not important: creams, lotions, ointments, milks, gels, emulsions, dispersions, solutions, suspensions, cleansers, foundations, anhydrous preparations (sticks, in particular lipsticks, body and bath oils), shower and bath gels, shampoos and scalp treatment lotions, cream or lotion for care of the skin or hair, sun-screen lotions, milks or creams, artificial suntan lotions, creams or milks, shaving creams or foams, aftershave lotions, make-up, mascaras or nail varnishes, lipsticks, skin "essences," serums, adhesive or absorbent materials, transdermal patches, powders, emollient lotion, emollient milk, emollient cream, sprays, oils for the body and the bath, foundation tint bases, pomade, emulsion, colloid, compact or solid suspension, pencil, sprayable formulation, brossable, rouge, blush, eyeliner, lipliner, lip gloss, facial or body powder, mousse, styling gels, nail conditioner, brush on formulation, lip balms, skin conditioners, cold creams, moisturizers, hair sprays, soaps, body scrubs, exfoliants, astringents, depilatories and permanent waving solutions, antidandruff formulations, anti-sweat and antiperspirant compositions, shaving, pre-shaving and after-shaving products, moisturizers, deodorants, cold creams, cleansers, skin gels, rinses, nose sprays and so on. These compositions can also be presented in the form of lipsticks intended to apply colour or to protect the lips from cracking, or of make-up products for the eyes or tints and tint bases for the face. Compositions in accordance with the present disclosure include cosmetics, personal care products and pharmaceutical preparations. One can also consider a composition in the shape of foam or in the form of compositions for aerosol also including a propellant agent under pressure.

In one embodiment of the current invention, light absorbing molecule such as phycocyanin and phycoerythrin, hereby also referred to as active light protection ingredient (s), are presented in solvents that is appropriate for maintaining the stability and photoabsorbing abilities of the active ingredients. The solution can be directly applied to the skin that is to be exposed to light such as sun rays. In another embodiment, the active ingredients are mixed with commonly used components of sunscreens including other active or inactive ingredients, or beauty products, or other cosmetic products. The mixtures, in liquid, semisolid, or paste forms, can be directly or indirectly (over a layer of material above the skin or other tissues) for preventing the damage caused by lights.

In another embodiment of the current invention, small biological molecules such as FMN, FAD, NAD, or other light-absorbing chemicals, particularly those with chromophores, are presented in solvents that is appropriate for maintaining the stability and photoabsorbing abilities of the active ingredients. The solution can be directly applied to the skin that is to be exposed to light such as sun rays. In another embodiment, the active ingredients are mixed with commonly used components of sunscreens including other active or inactive ingredients, or beauty products, or other cosmetic products. The mixtures, in liquid, semisolid, or paste forms, can be directly or indirectly (over a layer of material above the skin or other tissues) for preventing the damage caused by lights.

In another embodiment of the current invention, FPs from *Aequorea victoria* (jelly fish hydromedusa), various coral, other previous known species that naturally produce fluorescent proteins, and particularly those belonging to the lancelet FP families, are used as light absorbing molecules. They are used either as stand-alone products in appropriate solutions such as water, phosphate-buffered saline, Tris-buffered-saline, other storage forms such as lyophilized solid, or in combination with additional components as described above.

In one example of this embodiment, lancelet FPs (Lan FP) LanYFP (SEQ ID No. 1), LanRFP (SEQ ID No.2) are expressed and isolated in bacteria using recombinant protein expression methods that are commonly known in the art. The FP proteins in water or salt-based buffers such as PBS, Tris-based buffer, HEPES buffers etc. are directly applied to the skin prior to sun light exposure. After 10, 20, 30 min, or longer exposure to sun lights, the skins are examined to see if protective effects have been exerted by the recombinant LanFPs. Commercially available sunscreen products such as Neutrogena brand UltraSheer (Dry-Touch Sunblock with SPF 70) is used for comparison. Other brands and product lines may also be used. A further utilization can be realized by mixing the sunscreen product(s) with recombinant LanFPs at a ratio of 1:1,000, 1:100, 1:10, 1:1, 10:1, 100:1, or 1,000:1 or even higher or lower rations v:v LanFP to currently existing sunscreen products. An additional variation of the design of the invented products is to include FPs from non-lancelet FP families such as Allele Biotech's mTFP1 and mWasabi (previously described [8, 9], which are incorporated by reference herein). Fluorescent proteins that are from other origins including those created by protein engineering to mimic the natural FP structures that may or may not demonstrate absorbance/emission spectra from LanFPs can also be used and are incorporated herein by reference.

LanFPs to be used as components in the novel skin protection composition in the current invention can also be isolated directly from lancelets that are farmed or collected from the wild, or using other species after transgenic manipulations commonly known in the industry of protein production. Such species may be bacteria, yeasts, algae, plants, insects (or cultures of insect cells), mammals (or cultures of mammalian cells), etc. To isolate such proteins, various separation techniques such as centrifugation, precipitation in organic chemicals, chromatography, electrophoresis, and other methodologies known to a skilled worker in the art may be employed. Other FPs or proteins may be isolated or produced as recombinant proteins by biological and biochemical processes commonly practiced in the field of protein production and purification.

In yet another embodiment, other members of the Lancelet FP families, such as those with absorbing spectra in UVB, UVA, visible lights and emission spectra in various wavelengths, or are quenchers that do not emit lights in easily detectable ways, are used in place of or in addition to LanYFP and LanRFP as described in the examples.

In a further embodiment, these FPs, with different absorbing spectra, are used together to cover a wide or even a complete range of damaging lights that are to be prevented from reaching human tissues and causing damages.

In a related embodiment, multiple FPs are further selected based on their colors for cosmetic purposes or to make the sunscreen products more appealing, pleasant, or attractive to various sub-populations such as kids, women, or people with different natural skin colors.

In an additional embodiment, FPs of the lancelet FP family, most of which are known to exist in tetramers, are induced to form heterotetramers, trimers, or dimers for different light absorbing, colors, and/or energy-transfer properties. The mixed, or heteropolymers can be used as light protection reagents or components.

In another embodiment, wildtype FPs are mutated to create novel proteins that may possess properties not shared by the naturally occurring proteins. The mutant proteins may be used as light protection reagents or components of such products.

EXAMPLES

Example 1—Testing of Room Temperature Storage of Fluorescent Proteins

PLASMIDS that were constructed for bacterial expression of mTFP1 (Allele Biotech), mWasabi (Allele Biotech), mTangerine, and mCherry were expressed in DH5a *E. coli* bacteria. The bacterial cells were left in the original LB medium in 15 ml conical tubes at room temperature (RT) for 18 months. FPs released from the cells remain fluorescent during the entire time (FIG. 1), indicating that their 11-beta-barrell structure remained intact during extended storage without stabilizing reagents and in the probable presence of proteases released from bacteria.

Example 2—Cloning of Lanyfp and Lanrfp

LANYFP and LanRFP cDNA plasmids were provided by Dr. Olle Israelsson of the Department of Microbiology, Tumor and Cell Biology, Karolinska Institutet, Sweden. PCR primers designed to amply the complete coding regions of the FPs were synthesized at Allele Biotech and used to amply the fragments of predicted sizes. Through multiple steps using molecular biology techniques known in the art, the DNA fragments that encode the desired proteins, which were designed to have a few minor changes from the wildtype lancelet proteins, were cloned between BamHI and EcoRI sites of the bacterial expression vector pNCS (Allele Biotech).

Example 3—Preparation and Characterization of lanYFP and lanRFP Recombinant Proteins in *E. coli*

The RESULTING plasmids from Example 2 experiments were used for producing His-tagged recombinant proteins in the DH5a strain of *E. coli* by standard procedures known to a skilled artisan. FIG. 2 showed examples of such proteins purified by this method.

The stability of the recombinant proteins in terms of their abilities to maintain their native physical structures for excitation and emission was further tested. This was an important indicator for their use in photo absorbance and light damage prevention in skincare or sunscreen products. The wildtype lancelet FPs were known to form tight tetramers. The stability of the FPs was tested by running the recombinant proteins through denaturing electrophoresis, which is commonly known as SDS-PAGE in the field. As shown in FIG. 3, a significant amount of both the LanYFP and LanRFP remained in tetrameric forms and were strongly fluorescent. For comparison, a known monomeric FP, mTFP1, ran as a monomer, as demonstrated by a faster migration on the gel.

Example 4—Using of FPs for Photoprotection

About 100 microliter of the LanFP-containing solutions from Example 3 (FIG. 2) was applied to the skin on the chest or forearms of volunteers. After 30 minutes of outdoor activities under direct sun lights, there was a visible spots of less skin darkening where the LanFPs were applied.

Example 5—Use of FPs for Photoprotection as Part of Sunscreen

LanFPs in solutions were mixed with exemplary commercially available sunscreen such as Netutrogena brand UltraSheer Dry-Touch Sunblock with SPF 70 before it was applied to skin areas as described in Example 4. Sunscreen alone was used as a control. After about 2 hours of outdoor activity, the areas with different protectants were visually inspected and compared. There was a discernable difference between the control area and the test area, with the LanFP-containing test area having less sunburn and discoloration.

Sunburn, although not a disease or of severe consequences, was used as an indicator of UVB damage and for assessment of the effectiveness of sunscreen products.

Example 6—Optimization and Formation of Heterotetramers of Lanfps for Energy Transfer The naturally occurring lancelet FPs family account for more than a dozen FPs in one species, thus, the protein family family can cover a wide range of the light spectrum. We demonstrated that by mixing different FPs to form heterotetramers, i.e. tetramers formed by closely related but non-identical LanFPs resulted in combinations that possessed additional photophysical properties such as having maximum absorbance in additional wavelengths. Purified LanYFP, LanRFP, and control mTFP1 were mixed at 1:1 ratio; half of the mixtures were then transferred to another set of tubes. One set of the mixtures was left at room temperature; the second set was stored at −80 C for 2 hours. Pictures were taken immediately after taking the tubes from −80 C and placed next to the room temperature mixture set. After freezing, the FP tetramers was excluded from the water phase, possibly due to the strong hydrophobic interfaces between tetramer subunits, the fluorescence had a different appearance than the parental, unmixed LanFP (FIG. 4), indicating the possibility of heterotetramer formation through this simple freezing process.

Example 7—In Vitro Demonstration of the Efficacy of Fluorescent Proteins in Reducing Cell Toxicity Caused by UV Irridiation Equal amount of LanRFP, LanYFP, and mWasabi were tested for protection against cell killing by shortwave UV. Bovine Serum Albumin (BSA) was used as a control protein. Approximately 5 microgram of each protein, as determined by a Bradford assay performed using a SpectraMax plate reader, was added into the medium of human cells related to the 293T cell line which had been grown in 96-well plate for approximately 24 hours. UV light exposure was conducted by placing a Model UVGL-58 Mineralight Lamp set at UV-254 nm roughly 1 cm above the cells for various time intervals. FIG. 5 showed the results of one exemplary experiment that the cells were exposed to UV for 5 minutes inside a tissue culture hood at ambient temperature. The pictures of the treated cells shown in FIG. 5 were taken 24 hours post UV-treatment. The resultant image clearly demonstrated that fluorescent proteins, particularly LanRFP, which has an absorbance peak near 254 nm, had a significant effect in protecting cells from being killed by UV light. For comparison, without UV exposure, cells grown in medium with added FPs or BSA grew at a very similar rate without detectable cell death, thus demonstrating that addition of FPs did not cause cell growth abnormality or toxicity.

REFERENCES

1. Pleasance, E. D., R. K. Cheetham, P. J. Stephens, D. J. McBride, S. J. Humphray, C. D. Greenman, I. Varela, M. L. Lin, G. R. Ordonez, G. R. Bignell, K. Ye, J. Alipaz, M. J. Bauer, D. Beare, A. Butler, R. J. Carter, L. Chen, A. J. Cox, S. Edkins, P. I. Kokko-Gonzales, N. A. Gormley, R. J. Grocock, C. D. Haudenschild, M. M. Hims, T. James, M. Jia, Z. Kingsbury, C. Leroy, J. Marshall, A. Menzies, L. J. Mudie, Z. Ning, T. Royce, O. B. Schulz-Trieglaff, A. Spiridou, L. A. Stebbings, L. Szajkowski, J. Teague, D. Williamson, L. Chin, M. T. Ross, P. J. Campbell, D. R. Bentley, P. A. Futreal, and M. R. Stratton, *A comprehensive catalogue of somatic mutations from a human cancer genome*. Nature. 463(7278): p. 191-6.
2. Botta, C., C. Di Giorgio, A. S. Sabatier, and M. De Meo, Genotoxicity of visible light (400-800 nm) and photoprotection assessment of ectoin, L-ergothioneine and mannitol and four sunscreens. J Photochem Photobiol B, 2008. 91(1): p. 24-34.
3. Bou-Abdallah, F., N. D. Chasteen, and M. P. Lesser, *Quenching of superoxide radicals by green fluorescent protein*. Biochim Biophys Acta, 2006. 1760(11): p. 1690-5.

4. Palmer, C. V., C. K. Modi, and L. D. Mydlarz, *Coral fluorescent proteins as antioxidants*. PLoS One, 2009. 4(10): p. e7298.
5. Hoi, H., N. C. Shaner, M. W. Davidson, C. W. Cairo, J. Wang, and R. E. Campbell, A Monomeric Photoconvertible Fluorescent Protein for Imaging of Dynamic Protein Localization. J Mol Biol.
6. Deheyn, D. D., K. Kubokawa, J. K. McCarthy, A. Murakami, M. Porrachia, G. W. Rouse, and N. D. Holland, *Endogenous green fluorescent protein (GFP) in amphioxus*. Biol Bull, 2007. 213(2): p. 95-100.
7. Bomati, E. K., G. Manning, and D. D. Deheyn, Amphioxus encodes the largest known family of green fluorescent proteins, which have diversified into distinct functional classes. BMC Evol Biol, 2009. 9: p. 77.
8. Ai, H. W., J. N. Henderson, S. J. Remington, and R. E. Campbell, Directed evolution of a monomeric, bright and photostable version of Clavularia cyan fluorescent protein: structural characterization and applications in fluorescence imaging. Biochem J, 2006. 400(3): p. 531-40.
9. Ai, H. W., S. G. Olenych, P. Wong, M. W. Davidson, and R. E. Campbell, Hue-shifted monomeric variants of Clavularia cyan fluorescent protein: identification of the molecular determinants of color and applications in fluorescence imaging. BMC Biol, 2008. 6: p. 13.

SEQUENCE LISTING

```
<160> NUMBER OF SEQ ID NOS: 16

<210> SEQ ID NO 1
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggtgagca agggcgagga ggataacatg gcctctctcc cagcgacaca tgagttacac      60
atctttggct ccttcaacgg tgtggacttt gacatggtgg tcgtggcac cggcaatcca     120 aatgatggtt atgaggagtt aaacctgaag tccaccaagg gtgccctcca gttctccccc    180
tggattctgg tccctcaaat cgggtatggc ttccatcagt acctgccctt ccccgacggg    240
atgtcgcctt tccaggccgc catgaaagat ggctccggat accaagtcca tcgcacaatg    300
cagtttgaag acggtgcctc cctgacttcc aactaccgct acacctacga gggaagccac    360
atcaaaggag agtttcaggt gatcgggact ggtttccctg ctgacggtcc tgtgatgacc    420
aactcgctga ccgctgcgga ctggtgcgtg accaagatgc tgtaccccaa cgacaaaacc    480
atcatcagca cctttgactg gacttacacc actggaagtg gcaagcgcta ccagagcaca    540
gtgcggacca actacacctt tgccaagcca atggcggcca acatcctgaa gaaccagccg    600
atgttcgtgt tccgtaagac ggagctcaag cactccaaga ccgagctcaa cttcaaggag    660
tggcaaaagg cctttaccga tgtgatgggc atggacgagc tgtacaag              708

<210> SEQ ID NO 2
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggtgagca agggcgagga ggataacatg gcccctctcc cagcaaccca cgatttacac      60
atctccggct caatcaatgg acatgagttt gacttggaag gcagtggcaa gggcaatgca    120
aaagaaggtt atcaggagct ccacctaaag tccaacaagg gtgacctgtc attctccccc    180
tggattctgg tcccaaacat cggctacggc ttctaccagt acctgccctt ccccgacgga    240
gcgatgtcgc cttaccaggc cgccatgcac gatggctccg gatacgtgat gcatcgttca    300
atgcagtttg aggatggtgc catgctgcat tcagaccacc gctacatcta taaggggaaac    360 catatcaaag gagagtttcg gctgaccgga agcggttttcc ctgctgacgg ccctgtgatg    420
```

```
accaactcgc tgaccgctgc ggactggtgc gtcgacaagc tgctgtaccc aaacgacaac      480
accataatcg gcaaattcga ctggacctac accactacca gtggcaagcg ctaccaaagt      540
gatgtgcaga ccaacgtcac atttggcaag ccaatagcgg ccgacatttt gaagaagcag      600
ccaatgttcg tgttccgcaa ggtggaactc aagcacacca agactgagct caacttcaag      660
cagtggcaga aggcattcca ggacatcgcc ggcatggacg agctgtacaa gtaattaatg      720
cag                                                                    723
```

<210> SEQ ID NO 3
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Val Ser Lys Gly Glu Glu Asp Asn Met Ala Ser Leu Pro Ala Thr
1               5                   10                  15

His Glu Leu His Ile Phe Gly Ser Phe Asn Gly Val Asp Phe Asp Met
            20                  25                  30

Val Gly Arg Gly Thr Gly Asn Pro Asn Asp Gly Tyr Glu Glu Leu Asn
        35                  40                  45

Leu Lys Ser Thr Lys Gly Ala Leu Gln Phe Ser Pro Trp Ile Leu Val
    50                  55                  60

Pro Gln Ile Gly Tyr Gly Phe His Gln Tyr Leu Pro Phe Pro Asp Gly
65                  70                  75                  80

Met Ser Pro Phe Gln Ala Ala Met Lys Asp Gly Ser Gly Tyr Gln Val
                85                  90                  95

His Arg Thr Met Gln Phe Glu Asp Gly Ala Ser Leu Thr Ser Asn Tyr
            100                 105                 110

Arg Tyr Thr Tyr Glu Gly Ser His Ile Lys Gly Glu Phe Gln Val Ile
        115                 120                 125

Gly Thr Gly Phe Pro Ala Asp Gly Pro Val Met Thr Asn Ser Leu Thr
    130                 135                 140

Ala Ala Asp Trp Cys Val Thr Lys Met Leu Tyr Pro Asn Asp Lys Thr
145                 150                 155                 160

Ile Ile Ser Thr Phe Asp Trp Thr Tyr Thr Thr Gly Ser Gly Lys Arg
                165                 170                 175

Tyr Gln Ser Thr Val Arg Thr Asn Tyr Thr Phe Ala Lys Pro Met Ala
            180                 185                 190

Ala Asn Ile Leu Lys Asn Gln Pro Met Phe Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235
```

<210> SEQ ID NO 4
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Val Ser Lys Gly Glu Glu Asp Asn Met Ala Pro Leu Pro Ala Thr
1               5                   10                  15

His Asp Leu His Ile Ser Gly Ser Ile Asn Gly His Glu Phe Asp Leu
            20                  25                  30

Glu Gly Ser Gly Lys Gly Asn Ala Lys Glu Gly Tyr Gln Glu Leu His
        35                  40                  45

Leu Lys Ser Asn Lys Gly Asp Leu Ser Phe Ser Pro Trp Ile Leu Val
50                  55                  60

Pro Asn Ile Gly Tyr Gly Phe Tyr Gln Tyr Leu Pro Phe Pro Asp Gly
65                  70                  75                  80

Ala Met Ser Pro Tyr Gln Ala Ala Met His Asp Gly Ser Gly Tyr Val
                85                  90                  95

Met His Arg Ser Met Gln Phe Glu Asp Gly Ala Met Leu His Ser Asp
            100                 105                 110

His Arg Tyr Ile Tyr Lys Gly Asn His Ile Lys Gly Glu Phe Arg Leu
            115                 120                 125

Thr Gly Ser Gly Phe Pro Ala Asp Gly Pro Val Met Thr Asn Ser Leu
        130                 135                 140

Thr Ala Ala Asp Trp Cys Val Asp Lys Leu Leu Tyr Pro Asn Asp Asn
145                 150                 155                 160

Thr Ile Ile Gly Lys Phe Asp Trp Thr Tyr Thr Thr Ser Gly Lys
                165                 170                 175

Arg Tyr Gln Ser Asp Val Gln Thr Asn Val Thr Phe Gly Lys Pro Ile
            180                 185                 190

Ala Ala Asp Ile Leu Lys Lys Gln Pro Met Phe Val Phe Arg Lys Val
            195                 200                 205

Glu Leu Lys His Thr Lys Thr Glu Leu Asn Phe Lys Gln Trp Gln Lys
210                 215                 220

Ala Phe Gln Asp Ile Ala Gly Met Asp Glu Leu Tyr Lys
225                 230                 235
```

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Thr Thr Lys Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Thr Thr Lys Ser
1               5

<210> SEQ ID NO 7
<211> LENGTH: 236
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 7

Met Val Ser Lys Gly Glu Glu Asp Asn Met Ala Ser Leu Pro Ala Thr
1               5                   10                  15

His Glu Leu His Ile Phe Gly Ser Phe Asn Gly Val Asp Phe Asp Met
            20                  25                  30

Val Gly Glu Gly Thr Gly Asn Pro Asn Asp Gly Tyr Glu Glu Leu Asn
        35                  40                  45

Leu Lys Trp Thr Lys Gly Pro Leu Gln Gly Tyr Gly Phe His Leu Val
    50                  55                  60

Pro Gln Ile Gly Tyr Gly Phe His Gln Tyr Leu Pro Phe Pro Asp Gly
65                  70                  75                  80

Met Ser Pro Phe Gln Ala Ala Met Lys Asp Gly Ser Gly Tyr Gln Val
                85                  90                  95

His Arg Thr Met Gln Tyr Glu Asp Gly Ala Ser Leu Thr Ser Asn Tyr
            100                 105                 110

Arg Tyr Thr Tyr Glu Gly Ser His Ile Lys Gly Glu Phe Gln Val Ile
        115                 120                 125

Gly Thr Gly Phe Pro Ala Asp Gly Pro Val Met Thr Asn Ser Leu Thr
    130                 135                 140

Ala Ala Asp Trp Cys Val Thr Lys Met Leu Tyr Pro Trp Asp Tyr Thr
145                 150                 155                 160

Ile Ile Ser Thr Phe Asp Trp Thr Tyr Thr Thr Gly Ser Gly Lys Arg
                165                 170                 175

Tyr Gln Ser Thr Val Arg Thr Asn Tyr Thr Phe Ala Lys Pro Met Ala
            180                 185                 190

Ala Asn Arg Leu Lys Asn Gln Pro Met Phe Val Phe Arg Lys Thr Glu
        195                 200                 205

Leu Glu His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 8
<211> LENGTH: 237
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 8

Met Val Ser Lys Gly Glu Glu Asp Asn Met Ala Pro Leu Pro Ala Thr
1               5                   10                  15

His Asp Leu His Ile Ser Gly Ser Ile Asn Gly His Glu Phe Asp Leu
            20                  25                  30

Glu Gly Gln Gly Lys Gly Asn Ala Lys Glu Gly Tyr Gln Glu Leu His
        35                  40                  45

Leu Lys Trp Asn Lys Gly Pro Leu Ser Gly Tyr Gly Phe Tyr Leu Val
    50                  55                  60

Pro Asn Ile Gly Tyr Gly Phe Tyr Gln Tyr Leu Pro Phe Pro Asp Gly
65                  70                  75                  80

Ala Met Ser Pro Tyr Gln Ala Ala Met His Asp Gly Ser Gly Tyr Val
                85                  90                  95

```
Met His Arg Ser Met Gln His Glu Asp Gly Ala Met Leu His Ser Asp
            100                 105                 110

His Arg Tyr Ile Tyr Lys Gly Asn His Ile Lys Gly Glu Phe Arg Leu
        115                 120                 125

Thr Gly Ser Gly Phe Pro Ala Asp Gly Pro Val Met Thr Asp Ser Leu
    130                 135                 140

Thr Ala Ala Asp Trp Cys Val Asp Lys Leu Leu Tyr Pro Trp Asp Tyr
145                 150                 155                 160

Thr Ile Ile Gly Lys Phe Asp Trp Thr Tyr Thr Thr Thr Ser Gly Lys
                165                 170                 175

Arg Tyr Gln Ser Asp Val Gln Thr Asn Val Thr Phe Gly Lys Pro Ile
            180                 185                 190

Ala Ala Asp Arg Leu Lys Lys Gln Pro Met Phe Val Phe Arg Lys Val
        195                 200                 205

Glu Leu Gln His Thr Lys Thr Glu Leu Asn Phe Lys Gln Trp Gln Lys
    210                 215                 220

Ala Phe Gln Asp Ile Ala Gly Met Asp Glu Leu Tyr Lys
225                 230                 235
```

<210> SEQ ID NO 9
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
tctctcccag cgacacatga gttacacatc tttggctcct tcaacggtgt ggactttgac      60
atggtgggtc gtggcaccgg caatccaaat gatggttatg aggagttaaa cctgaagtcc     120
accaagggtg ccctccagtt ctcccccctgg attctggtcc tcaaatcgg gtatggcttc     180
catcagtacc tgccctttcc cgacgggatg tcgccttttcc aggccgccat gaaagatggc     240
tccggatacc aagtccatcg cacaatgcag tttgaagacg gtgcctccct gacttccaac     300
taccgctaca cctacgaggg aagccacatc aaaggagagt tcaggtgat cgggactggt     360
ttccctgctg acggtcctgt gatgaccaac tcgctgaccg ctgcggactg gtgcgtgacc     420
aagatgctgt accccaacga caaaaccatc atcagcacct ttgactggac ttacaccact     480
ggaagtggca agcgctacca gagcacagtg cggaccaact acacctttgc caagccaatg     540
gcggccaaca tcctgaagaa ccagccgatg ttcgtgttcc gtaagacgga gctcaagcac     600
tccaagaccg agctcaactt caaggagtgg caaaaggcct ttaccgatgt gatgggcatg     660
gacgagctgt acaag                                                    675
```

<210> SEQ ID NO 10
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
cctctcccag caacccacga tttacacatc tccggctcaa tcaatggaca tgagtttgac      60
ttggaaggca gtggcaaggg caatgcaaaa gaaggttatc aggagctcca cctaaagtcc     120
aacaagggtg acctgtcatt ctccccctgg attctggtcc caaacatcgg ctacggcttc     180
```

| | |
|---|---|
| taccagtacc tgcccttccc cgacggagcg atgtcgcctt accaggccgc catgcacgat | 240 |
| ggctccggat acgtgatgca tcgttcaatg cagtttgagg atggtgccat gctgcattca | 300 |
| gaccaccgct acatctataa gggaaaccat atcaaaggag agtttcggct gaccggaagc | 360 |
| ggtttccctg ctgacggccc tgtgatgacc aactcgctga ccgctgcgga ctggtgcgtc | 420 |
| gacaagctgc tgtacccaaa cgacaacacc ataatcggca aattcgactg gacctacacc | 480 |
| actaccagtg gcaagcgcta ccaaagtgat gtgcagacca acgtcacatt tgcaagcca | 540 |
| atagcggccg acattttgaa gaagcagcca atgttcgtgt tccgcaaggt ggaactcaag | 600 |
| cacaccaaga ctgagctcaa cttcaagcag tggcagaagg cattccagga catcgccggc | 660 |
| atggacgagc tgtacaagta attaatgcag | 690 |

<210> SEQ ID NO 11
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Leu Pro Ala Thr His Glu Leu His Ile Phe Gly Ser Phe Asn Gly
1               5                   10                  15

Val Asp Phe Asp Met Val Gly Arg Gly Thr Gly Asn Pro Asn Asp Gly
            20                  25                  30

Tyr Glu Glu Leu Asn Leu Lys Ser Thr Lys Gly Ala Leu Gln Phe Ser
        35                  40                  45

Pro Trp Ile Leu Val Pro Gln Ile Gly Tyr Gly Phe His Gln Tyr Leu
    50                  55                  60

Pro Phe Pro Asp Gly Met Ser Pro Phe Gln Ala Ala Met Lys Asp Gly
65                  70                  75                  80

Ser Gly Tyr Gln Val His Arg Thr Met Gln Phe Glu Asp Gly Ala Ser
                85                  90                  95

Leu Thr Ser Asn Tyr Arg Tyr Thr Tyr Glu Gly Ser His Ile Lys Gly
            100                 105                 110

Glu Phe Gln Val Ile Gly Thr Gly Phe Pro Ala Asp Gly Pro Val Met
        115                 120                 125

Thr Asn Ser Leu Thr Ala Ala Asp Trp Cys Val Thr Lys Met Leu Tyr
    130                 135                 140

Pro Asn Asp Lys Thr Ile Ile Ser Thr Phe Asp Trp Thr Tyr Thr Thr
145                 150                 155                 160

Gly Ser Gly Lys Arg Tyr Gln Ser Thr Val Arg Thr Asn Tyr Thr Phe
                165                 170                 175

Ala Lys Pro Met Ala Ala Asn Ile Leu Lys Asn Gln Pro Met Phe Val
            180                 185                 190

Phe Arg Lys Thr Glu Leu Lys His Ser Lys Thr Glu Leu Asn Phe Lys
        195                 200                 205

Glu Trp Gln Lys Ala Phe Thr Asp Val Met Gly Met Asp Glu Leu Tyr
    210                 215                 220

Lys
225

<210> SEQ ID NO 12
<211> LENGTH: 226
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 12

Pro Leu Pro Ala Thr His Asp Leu His Ile Ser Gly Ser Ile Asn Gly
1               5                   10                  15

His Glu Phe Asp Leu Glu Gly Ser Gly Lys Gly Asn Ala Lys Glu Gly
            20                  25                  30

Tyr Gln Glu Leu His Leu Lys Ser Asn Lys Gly Asp Leu Ser Phe Ser
        35                  40                  45

Pro Trp Ile Leu Val Pro Asn Ile Gly Tyr Gly Phe Tyr Gln Tyr Leu
50                  55                  60

Pro Phe Pro Asp Gly Ala Met Ser Pro Tyr Gln Ala Ala Met His Asp
65                  70                  75                  80

Gly Ser Gly Tyr Val Met His Arg Ser Met Gln Phe Glu Asp Gly Ala
                85                  90                  95

Met Leu His Ser Asp His Arg Tyr Ile Tyr Lys Gly Asn His Ile Lys
            100                 105                 110

Gly Glu Phe Arg Leu Thr Gly Ser Gly Phe Pro Ala Asp Gly Pro Val
        115                 120                 125

Met Thr Asn Ser Leu Thr Ala Ala Asp Trp Cys Val Asp Lys Leu Leu
130                 135                 140

Tyr Pro Asn Asp Asn Thr Ile Ile Gly Lys Phe Asp Trp Thr Tyr Thr
145                 150                 155                 160

Thr Thr Ser Gly Lys Arg Tyr Gln Ser Asp Val Gln Thr Asn Val Thr
                165                 170                 175

Phe Gly Lys Pro Ile Ala Ala Asp Ile Leu Lys Lys Gln Pro Met Phe
            180                 185                 190

Val Phe Arg Lys Val Glu Leu Lys His Thr Lys Thr Glu Leu Asn Phe
        195                 200                 205

Lys Gln Trp Gln Lys Ala Phe Gln Asp Ile Ala Gly Met Asp Glu Leu
210                 215                 220

Tyr Lys
225

<210> SEQ ID NO 13
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Leu Pro Ala Thr His Glu Leu His Ile Phe Gly Ser Phe Asn Gly
1               5                   10                  15

Val Asp Phe Asp Met Val Gly Arg Gly Thr Gly Asn Pro Asn Asp Gly
            20                  25                  30

Tyr Glu Glu Leu Asn Leu Lys Ser Thr Lys Gly Ala Glu Gln Phe Ser
        35                  40                  45

Pro Trp Ile Leu Val Pro Gln Ile Gly Tyr Gly Phe Trp Gln Tyr Leu
50                  55                  60

Pro Phe Pro Gly Tyr Gly Phe His Phe Gln Ala Ala Met Lys Asp Gly
65                  70                  75                  80

Ser Gly Tyr Gln Val His Arg Thr Met Gln Phe Glu Asp Gly Ala Ser
                85                  90                  95
```

```
Leu Thr Ser Asn Tyr Arg Tyr Thr Tyr Glu Gly Ser His Ile Lys Tyr
            100                 105                 110

Glu Phe Gln Val Ile Gly Thr Gly Phe Pro Ala Asp Gly Pro Val Met
            115                 120                 125

Thr Asn Ser Leu Thr Ala Ala Asp Trp Cys Val Thr Lys Met Leu Tyr
130                 135                 140

Pro Asn Asp Lys Thr Ile Ile Ser Thr Phe Asp Trp Thr Tyr Thr Thr
145                 150                 155                 160

Gly Ser Gly Lys Arg Tyr Trp Ser Tyr Val Arg Thr Asn Tyr Thr Phe
            165                 170                 175

Ala Lys Pro Met Ala Ala Asn Ile Leu Lys Asn Gln Pro Met Phe Val
            180                 185                 190

Phe Arg Lys Thr Glu Leu Lys His Ser Lys Thr Glu Arg Asn Phe Lys
            195                 200                 205

Glu Trp Gln Lys Ala Phe Thr Asp Val Met Gly Glu Asp Glu Leu Tyr
            210                 215                 220

Lys
225

<210> SEQ ID NO 14
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Pro Leu Pro Ala Thr His Asp Leu His Ile Ser Gly Ser Ile Asn Gly
1               5                   10                  15

His Glu Phe Asp Leu Glu Gly Ser Gly Lys Gly Asn Ala Lys Glu Gly
            20                  25                  30

Tyr Gln Glu Leu His Leu Lys Ser Asn Lys Gly Asp Gln Ser Phe Ser
        35                  40                  45

Pro Trp Ile Leu Val Pro Asn Ile Gly Tyr Gly Phe Trp Gln Tyr Leu
50                  55                  60

Pro Phe Pro Gly Tyr Gly Phe Tyr Pro Tyr Gln Ala Ala Met His Asp
65                  70                  75                  80

Gly Ser Gly Tyr Val Met His Arg Ser Met Gln Phe Glu Asp Gly Ala
            85                  90                  95

Met Leu His Ser Asp His Arg Tyr Ile Tyr Lys Gly Asn His Ile Lys
            100                 105                 110

His Glu Phe Arg Leu Thr Gly Ser Gly Phe Pro Ala Asp Gly Pro Val
            115                 120                 125

Met Thr Asn Ser Leu Thr Ala Ala Asp Trp Cys Val Asp Lys Leu Leu
130                 135                 140

Tyr Pro Asn Asp Asn Thr Ile Asp Gly Lys Phe Asp Trp Thr Tyr Thr
145                 150                 155                 160

Thr Thr Ser Gly Lys Arg Tyr Trp Ser Tyr Val Gln Thr Asn Val Thr
            165                 170                 175

Phe Gly Lys Pro Ile Ala Ala Asp Ile Leu Lys Lys Gln Pro Met Phe
            180                 185                 190

Val Phe Arg Lys Val Glu Leu Lys His Thr Lys Thr Glu Arg Asn Phe
            195                 200                 205

Lys Gln Trp Gln Lys Ala Phe Gln Asp Ile Ala Gly Gln Asp Glu Leu
```

-continued

```
              210                 215                 220

Tyr Lys
225

<210> SEQ ID NO 15
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(44)
<223> OTHER INFORMATION: Any amino acid
<220> FEATURE:
<221> NAME/KEY: MOD_RES
<222> LOCATION: (46)..(60)
<223> OTHER INFORMATION: Any amino acid
<220> FEATURE:
<221> NAME/KEY: MOD_RES
<222> LOCATION: (62)..(64)
<223> OTHER INFORMATION: Any amino acid
<220> FEATURE:
<221> NAME/KEY: MOD_RES
<222> LOCATION: (66)..(67)
<223> OTHER INFORMATION: Any amino acid
<220> FEATURE:
<221> NAME/KEY: MOD_RES
<222> LOCATION: (73)..(111)
<223> OTHER INFORMATION: Any amino acid
<220> FEATURE:
<221> NAME/KEY: MOD_RES
<222> LOCATION: (113)..(166)
<223> OTHER INFORMATION: Any amino acid
<220> FEATURE:
<221> NAME/KEY: MOD_RES
<222> LOCATION: (168)..(168)
<223> OTHER INFORMATION: Any amino acid
<220> FEATURE:
<221> NAME/KEY: MOD_RES
<222> LOCATION: (170)..(204)
<223> OTHER INFORMATION: Any amino acid
<220> FEATURE:
<221> NAME/KEY: MOD_RES
<222> LOCATION: (206)..(219)
<223> OTHER INFORMATION: Any amino acid
<220> FEATURE:
<221> NAME/KEY: MOD_RES
<222> LOCATION: (221)..(225)
<223> OTHER INFORMATION: Any amino acid

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Glu Xaa Xaa Xaa
        35                  40                  45

Xaa Xaa Xaa Xaa Xaa Xaa Xaa Xaa Xaa Xaa Xaa Xaa Trp Xaa Xaa Xaa
    50                  55                  60

Pro Xaa Xaa Gly Tyr Gly Phe His Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Tyr
            100                 105                 110

Xaa Xaa Xaa Xaa Xaa Xaa Xaa Xaa Xaa Xaa Xaa Xaa Xaa Xaa Xaa Xaa
        115                 120                 125
```

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Trp Xaa Tyr Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Arg Xaa Xaa Xaa
        195                 200                 205

Xaa Xaa Xaa Xaa Xaa Xaa Xaa Xaa Xaa Xaa Glu Xaa Xaa Xaa Xaa
    210                 215                 220

Xaa
225

<210> SEQ ID NO 16
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(44)
<223> OTHER INFORMATION: Any amino acid
<220> FEATURE:
<221> NAME/KEY: MOD_RES
<222> LOCATION: (46)..(60)
<223> OTHER INFORMATION: Any amino acid
<220> FEATURE:
<221> NAME/KEY: MOD_RES
<222> LOCATION: (62)..(64)
<223> OTHER INFORMATION: Any amino acid
<220> FEATURE:
<221> NAME/KEY: MOD_RES
<222> LOCATION: (66)..(67)
<223> OTHER INFORMATION: Any amino acid
<220> FEATURE:
<221> NAME/KEY: MOD_RES
<222> LOCATION: (73)..(112)
<223> OTHER INFORMATION: Any amino acid
<220> FEATURE:
<221> NAME/KEY: MOD_RES
<222> LOCATION: (114)..(151)
<223> OTHER INFORMATION: Any amino acid
<220> FEATURE:
<221> NAME/KEY: MOD_RES
<222> LOCATION: (153)..(167)
<223> OTHER INFORMATION: Any amino acid
<220> FEATURE:
<221> NAME/KEY: MOD_RES
<222> LOCATION: (169)..(169)
<223> OTHER INFORMATION: Any amino acid
<220> FEATURE:
<221> NAME/KEY: MOD_RES
<222> LOCATION: (171)..(205)
<223> OTHER INFORMATION: Any amino acid
<220> FEATURE:
<221> NAME/KEY: MOD_RES
<222> LOCATION: (207)..(220)
<223> OTHER INFORMATION: Any amino acid
<220> FEATURE:
<221> NAME/KEY: MOD_RES
<222> LOCATION: (222)..(225)
<223> OTHER INFORMATION: Any amino acid

<400> SEQUENCE: 16

Xaa Xaa Xaa Xaa Xaa Xaa Xaa Xaa Xaa Xaa Xaa Xaa Xaa Xaa Xaa
1               5                   10                  15

```
Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Gln Xaa Xaa Xaa
            35                  40                  45

Xaa Xaa Xaa Xaa Xaa Xaa Xaa Xaa Xaa Xaa Xaa Trp Xaa Xaa Xaa
            50                  55                  60

Pro Xaa Xaa Gly Tyr Gly Phe Tyr Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

His Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Asp Xaa Xaa Xaa Xaa Xaa Xaa Xaa
145                 150                 155                 160

Xaa Xaa Xaa Xaa Xaa Xaa Xaa Trp Xaa Tyr Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Arg Xaa Xaa
            195                 200                 205

Xaa Xaa Xaa Xaa Xaa Xaa Xaa Xaa Xaa Xaa Gln Xaa Xaa Xaa
            210                 215                 220

Xaa
225
```

I claim:

1. A method for protecting the skin from light damage in a subject in need thereof, comprising topically administering a formulation comprising a dermatologically acceptable carrier or a vehicle and a functional *Brachiostoma* light absorbing protein polypeptide comprising the sequence from the N-terminus:

```
                                         (SEQ ID NO: 15)
Xaa1-Xaa2-Xaa3-Xaa4-Xaa5-Xaa6-Xaa7-Xaa8-Xaa9-Xaa10-

Xaa11-Xaa12-Xaa13-Xaa14-Xaa15-Xaa16-Xaa17-Xaa18-

Xaa19-Xaa20-Xaa21-Xaa22-Xaa23-Xaa24-Xaa25-Xaa26-

Xaa27-Xaa28-Xaa29-Xaa30-Xaa31-Xaa32-Xaa33-Xaa34-

Xaa35-Xaa36-Xaa37-Xaa38-Xaa39-Xaa40-Xaa41-Xaa42-

Xaa43-Xaa44-Glu45-Xaa46-Xaa47-Xaa48-Xaa49-Xaa50-

Xaa51-Xaa52-Xaa53-Xaa54-Xaa55-Xaa56-Xaa57-Xaa58-

Xaa59-Xaa60-Trp61-Xaa62-Xaa63-Xaa64-Pro65-Xaa66-

Xaa67-Gly68-Tyr69-Gly70-Phe71-His72-Xaa73-Xaa74-

Xaa75-Xaa76-Xaa77-Xaa78-Xaa79-Xaa80-Xaa81-Xaa82-

Xaa83-Xaa84-Xaa85-Xaa86-Xaa87-Xaa88-Xaa89-Xaa90-

Xaa91-Xaa92-Xaa93-Xaa94-Xaa95-Xaa96-Xaa97-Xaa98-

Xaa99-Xaa100-Xaa101-Xaa102-Xaa103-Xaa104-Xaa105-

Xaa106-Xaa107-Xaa108-Xaa109-Xaa110-Xaa111-Tyr112-

Xaa113-Xaa114-Xaa115-Xaa116-Xaa117-Xaa118-Xaa119-

Xaa120-Xaa121-Xaa122-Xaa123-Xaa124-Xaa125-Xaa126-

Xaa127-Xaa128-Xaa129-Xaa130-Xaa131-Xaa132-Xaa133-

Xaa134-Xaa135-Xaa136-Xaa137-Xaa138-Xaa139-Xaa140-

Xaa141-Xaa142-Xaa143-Xaa144-Xaa145-Xaa146-Xaa147-

Xaa148-Xaa149-Xaa150-Xaa151-Xaa152-Xaa153-Xaa154-

Xaa155-Xaa156-Xaa157-Xaa158-Xaa159-Xaa160-Xaa161-

Xaa162-Xaa163-Xaa164-Xaa165-Xaa166-Trp167-Xaa168-

Tyr169-Xaa170-Xaa171-Xaa172-Xaa173-Xaa174-Xaa175-

Xaa176-Xaa177-Xaa178-Xaa179-Xaa180-Xaa181-Xaa182-

Xaa183-Xaa184-Xaa185-Xaa186-Xaa187-Xaa188-Xaa189-

Xaa190-Xaa191-Xaa192-Xaa193-Xaa194-Xaa195-Xaa196-

Xaa197-Xaa198-Xaa199-Xaa200-Xaa201-Xaa202-Xaa203-

Xaa204-Arg205-Xaa206-Xaa207-Xaa208-Xaa209-Xaa210-
```

-continued
Xaa211-Xaa212-Xaa213-Xaa214-Xaa215-Xaa216-Xaa217-

Xaa218-Xaa219-Glu220-Xaa221-Xaa222-Xaa223-Xaa224-

Xaa225, wherein the polypeptide sequence has no more than 5 substitutions to that of SEQ ID NO: 11 or SEQ ID NO: 12, wherein Xaa is any amino acid.

2. A method for protecting the skin from light damage in a subject in need thereof, comprising topically administering a formulation comprising a dermatologically acceptable carrier or a vehicle and a functional *Brachiostoma* light absorbing protein polypeptide specified by the sequence from the N-terminus:

(SEQ ID NO: 15)
Xaa Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Glu45 Xaa Xaa Xaa Xaa Xaa Xaa

Xaa Xaa Xaa Xaa Xaa Xaa Xaa Xaa Xaa Trp61 Xaa Xaa

Xaa Pro65 Xaa Xaa Gly68 Tyr69 Gly70 Phe71 His72 Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa

Tyr112 Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Trp167 Xaa Tyr169 Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Arg205 Xaa Xaa Xaa Xaa Xaa Xaa

Xaa Xaa Xaa Xaa Xaa Xaa Xaa Xaa Glu220 Xaa Xaa Xaa

Xaa Xaa, wherein the polypeptide sequence has no more than 5 substitutions to that of SEQ ID NO: 3 or SEQ ID NO: 4, wherein Xaa is any amino acid.

3. A method for protecting the skin from light damage in a subject in need thereof, comprising topically administering a formulation comprising a dermatologically acceptable carrier or a vehicle and a functional *Brachiostoma* light absorbing protein polypeptide specified by the sequence from the N-terminus:

(SEQ ID NO: 16)
Xaa Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa Xaa

-continued
Xaa Xaa Xaa Xaa Xaa Gln45 Xaa Xaa Xaa Xaa Xaa Xaa

Xaa Xaa Xaa Xaa Xaa Xaa Xaa Xaa Xaa Trp61 Xaa Xaa

Xaa Pro65 Xaa Xaa Gly68 Tyr69 Gly70 Phe71 Tyr72 Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

His113 Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Asp152 Xaa Xaa Xaa Xaa Xaa Xaa Xaa Xaa Xaa

Xaa Xaa Xaa Xaa Xaa Trp168 Xaa Tyr170 Xaa Xaa Xaa

Xaa Xaa Xaa Xaa Xaa Xaa Xaa Xaa Xaa Xaa Xaa Xaa

Xaa Xaa Xaa Xaa Xaa Xaa Xaa Xaa Xaa Xaa Xaa Xaa

Xaa Xaa Xaa Xaa Xaa Xaa Arg206 Xaa Xaa Xaa Xaa Xaa

Xaa Xaa Xaa Xaa Xaa Xaa Xaa Xaa Xaa Gln221 Xaa Xaa

Xaa Xaa, wherein the polypeptide sequence has no more than 5 substitutions to that of SEQ ID NO: 3 or SEQ ID NO: 4, wherein Xaa is any amino acid.

4. The method of any one of claim 1, 2, or 3 wherein the functional recombinant multimeric *Brachiostoma* light absorbing protein polypeptides formulated for topical administration comprises polypeptides that are tetramers, trimers or dimers.

5. The method of claim 4 wherein the functional recombinant *Brachiostoma* light absorbing protein polypeptides formulated for topical administration are tetramers.

6. The method of claim 4 wherein the recombinant multimeric protein is a heterotetrameric protein.

7. The method of claim 4 whereby administration of an effective amount of said formulation to said subject reduces UV-induced cellular damage in the subject.

8. The method of claim 1, wherein the polypeptide sequence has no more than 2 substitutions to that of SEQ ID NO: 11 or SEQ ID NO: 12.

9. The method of claim 2, wherein the polypeptide sequence has no more than 2 substitutions to that of SEQ ID NO: 3 or SEQ ID NO: 4.

10. The method of claim 3, wherein the polypeptide sequence has no more than 2 substitutions to that of SEQ ID NO: 11 or SEQ ID NO: 12.

11. A method for protecting the skin from light damage in a subject in need thereof, comprising topically administering a formulation comprising a dermatologically acceptable carrier or a vehicle and a plurality of functional *Brachiostoma* light absorbing protein polypeptides, wherein the functional *Brachiostoma* light absorbing protein polypeptides independently comprise the sequence from the N-terminus:

(SEQ ID NO: 15)
Xaa1-Xaa2-Xaa3-Xaa4-Xaa5-Xaa6-Xaa7-Xaa8-Xaa9-

-continued
Xaa10-Xaa11-Xaa12-Xaa13-Xaa14-Xaa15-Xaa16-Xaa17-
Xaa18-Xaa19-Xaa20-Xaa21-Xaa22-Xaa23-Xaa24-Xaa25-
Xaa26-Xaa27-Xaa28-Xaa29-Xaa30-Xaa31-Xaa32-Xaa33-
Xaa34-Xaa35-Xaa36-Xaa37-Xaa38-Xaa39-Xaa40-Xaa41-
Xaa42-Xaa43-Xaa44-Glu45-Xaa46-Xaa47-Xaa48-Xaa49-
Xaa50-Xaa51-Xaa52-Xaa53-Xaa54-Xaa55-Xaa56-Xaa57-
Xaa58-Xaa59-Xaa60-Trp61-Xaa62-Xaa63-Xaa64-Pro65-
Xaa66-Xaa67-Gly68-Tyr69-Gly70-Phe71-His72-Xaa73-
Xaa74-Xaa75-Xaa76-Xaa77-Xaa78-Xaa79-Xaa80-Xaa81-
Xaa82-Xaa83-Xaa84-Xaa85-Xaa86-Xaa87-Xaa88-Xaa89-
Xaa90-Xaa91-Xaa92-Xaa93-Xaa94-Xaa95-Xaa96-Xaa97-
Xaa98-Xaa99-Xaa100-Xaa101-Xaa102-Xaa103-Xaa104-
Xaa105-Xaa106-Xaa107-Xaa108-Xaa109-Xaa110-Xaa111-
Tyr112-Xaa113-Xaa114-Xaa115-Xaa116-Xaa117-Xaa118-
Xaa119-Xaa120-Xaa121-Xaa122-Xaa123-Xaa124-Xaa125-
Xaa126-Xaa127-Xaa128-Xaa129-Xaa130-Xaa131-Xaa132-
Xaa133-Xaa134-Xaa135-Xaa136-Xaa137-Xaa138-Xaa139-
Xaa140-Xaa141-Xaa142-Xaa143-Xaa144-Xaa145-Xaa146-
Xaa147-Xaa148-Xaa149-Xaa150-Xaa151-Xaa152-Xaa153-
Xaa154-Xaa155-Xaa156-Xaa157-Xaa158-Xaa159-Xaa160-
Xaa161-Xaa162-Xaa163-Xaa164-Xaa165-Xaa166-Trp167-
Xaa168-Tyr169-Xaa170-Xaa171-Xaa172-Xaa173-Xaa174-
Xaa175-Xaa176-Xaa177-Xaa178-Xaa179-Xaa180-Xaa181-
Xaa182-Xaa183-Xaa184-Xaa185-Xaa186-Xaa187-Xaa188-
Xaa189-Xaa190-Xaa191-Xaa192-Xaa193-Xaa194-Xaa195-
Xaa196-Xaa197-Xaa198-Xaa199-Xaa200-Xaa201-Xaa202-
Xaa203-Xaa204-Arg205-Xaa206-Xaa207-Xaa208-Xaa209-
Xaa210-Xaa211-Xaa212-Xaa213-Xaa214-Xaa215-Xaa216-
Xaa217-Xaa218-Xaa219-Glu220-Xaa221-Xaa222-Xaa223-
Xaa224-Xaa225, wherein the polypeptide sequence has no more than 5 substitutions to that of SEQ ID NO: 11 or SEQ ID NO: 12; or (SEQ ID NO: 15)
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Glu45 Xaa Xaa Xaa Xaa Xaa Xaa
Xaa Xaa Xaa Xaa Xaa Xaa Xaa Xaa Xaa Trp61 Xaa Xaa Xaa Pro65 Xaa Xaa Gly68 Tyr69 Gly70 Phe71 His72 Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa
Tyr112 Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Trp167 Xaa Tyr169 Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Arg205 Xaa Xaa Xaa Xaa Xaa
Xaa Xaa Xaa Xaa Xaa Xaa Xaa Xaa Xaa Glu220 Xaa Xaa
Xaa Xaa Xaa, wherein the polypeptide sequence has no more than 5 substitutions to that of SEQ ID NO: 3 or SEQ ID NO: 4; or (SEQ ID NO: 16)
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Gln45 Xaa Xaa Xaa Xaa Xaa Xaa
Xaa Xaa Xaa Xaa Xaa Xaa Xaa Xaa Xaa Trp61 Xaa Xaa
Xaa Pro65 Xaa Xaa Gly68 Tyr69 Gly70 Phe71 Tyr72 Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
His113 Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Asp152 Xaa Xaa Xaa Xaa Xaa Xaa Xaa Xaa Xaa Xaa
Xaa Xaa Xaa Xaa Xaa Trp168 Xaa Tyr170 Xaa Xaa Xaa
Xaa Xaa Xaa Xaa Xaa Xaa Xaa Xaa Xaa Xaa Xaa Xaa
Xaa Xaa Xaa Xaa Xaa Xaa Xaa Xaa Xaa Xaa Xaa Xaa
Xaa Xaa Xaa Xaa Xaa Arg206 Xaa Xaa Xaa Xaa Xaa Xaa
Xaa Xaa Xaa Xaa Xaa Xaa Xaa Xaa Xaa Gln221 Xaa Xaa
Xaa Xaa, wherein the polypeptide sequence no more than 5 substitutions to that of SEQ ID NO: 3 or SEQ ID NO: 4; wherein Xaa is any amino acid.

\* \* \* \* \*